Figure 2:
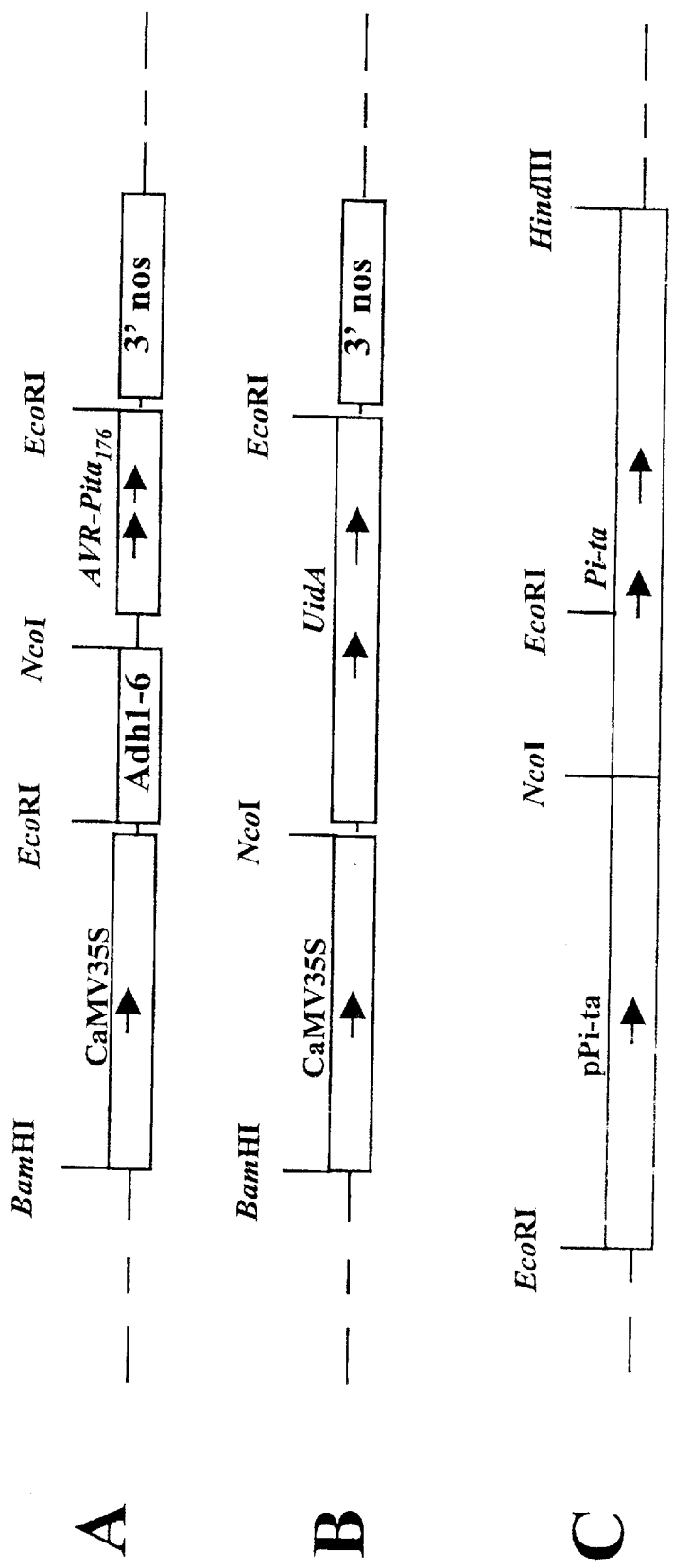
Figure 3:
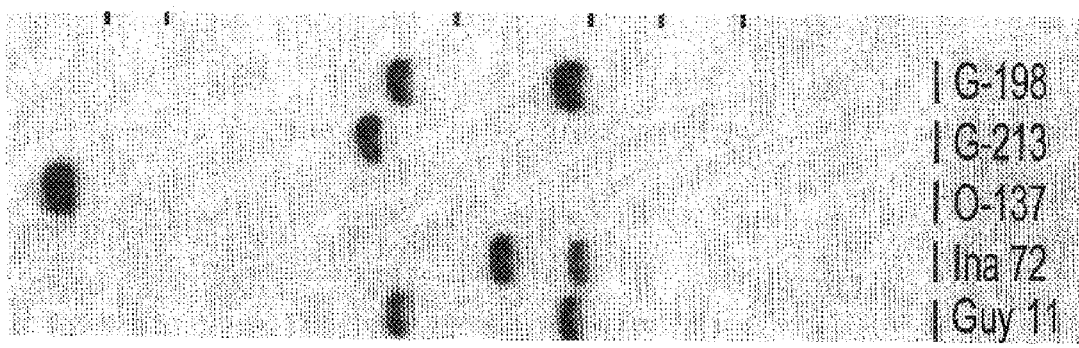

United States Patent
Bryan et al.

(10) Patent No.: US 6,743,969 B2
(45) Date of Patent: Jun. 1, 2004

(54) MODIFICATION OF PI-TA GENE CONFERRING FUNGAL DISEASE RESISTANCE TO PLANTS

(75) Inventors: Gregory Bryan, Palmerston North (NZ); Barbara Valent, Manhattan, KS (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/993,170

(22) Filed: Nov. 14, 2001

(65) Prior Publication Data

US 2002/0148004 A1 Oct. 10, 2002

Related U.S. Application Data

(60) Provisional application No. 60/248,335, filed on Nov. 14, 2000.

(51)

OTHER PUBLICATIONS

H. H. Flor, Annu. Rev. Phytopathol., vol. 9:275–296, 1971, Current Status of the Gene–for–Gene Concept.

Gregory B. Martin et. al., Science, vol. 262:1432–1436, 1993, MAP–Based Cloning of a Protein Kinase Gene Conferring Disease Resistance in Tomato.

Jonathan D.G. Jones, Adv. Bot. Res. Incorp. Adv. Plant Pathol. vol. 24:89–167, the Role of Leucine–Rich Repeat Proteins in Plant Defences.

David A. Jones et. al., Science, vol. 266:789–793, 1994, Isolation of the Tomato CF–9 Gene for Resistance to *Cladosporium fulvum* by Transposen Tagging.

Wen–Yuan Song et. al., Science, vol. 270:1804–1806, 1995, a Receptor Kinase–Like Protein Encoded by the Rice Disease Resistance Gene, XA21.

Andrew F. Bent et. al., Science, vol. 265:1856–1860, 1994, RPS2 of *Arabidopsis thaliana*: a Leucine–Rich Repeat Class of Plant Disease Resistance Genes.

Michael Mindrinos et. al., Cell, vol. 78:1089–1099, 1994, the *A. thaliana* Disease Resistance Gene RPS2 Encodes a Protein Containing a Nucleotide–Binding Site and Leucine–Rich Repeats.

Murray R. Grant et. al., Science, vol. 269:843–846, 1995, Structure of the Arabidopsis RPM1 Gene Enabling Dual Specificity Disease Resistance.

Barbara Baker et. al., Science, vol. 276:726–733, 1997, Signaling in Plant–Microbe Interactions.

Matti Saraste et. al., Trends in Biochem. Science, vol. 15:430–434, the P–Loop–A Common Motif in ATP—and GTP—Binding Proteins.

Thomas W. Traut, Eur. J. Biochem., vol. 222:9–19, 1994, the Functions and Consensus Motifs of Nine Types of Peptides Segments that Form Different Types of Nucleotide–Binding Sites.

Barbara Valent et. al., Genetics, vol. 127:87–101, 1991, *Magnaporthe grisea* Genes for Pathogenicity and Virulence Identified Through a Series of Backcrosses.

Drissa Silue et. al., Phytopathology, vol. 82:577–580, Evidence of a Gene–for–Gene Relationship in the *Oryza Sativa–Magnaporthe grisea* Pathosystem.

B. Valent, the Mycota V, Plant Relationships, Carroll/Tudzynski, Eds., Springer–Verlag Berlin Heidelberg, pp. 37–54., 1997, the Rice Blast Fungus, *Mapnaporthe grisea*.

A. S. Urashima et. al., Plant Disease, vol. 77:1211–1216, 1993, Host Range, Mating Type, and Fertility of *Pyricularia grisea* from Wheat in Brazil.

W. W. Hanna et. al., J. Heredity, vol. 80:145–147, 1989, Inheritance of Pyricularia Leaf Spot Resistance in Pearl Millet.

Rintaro Sasaki, Japanese Journal of Genetics, vol. 1:81–85, Inheritance of Resistance to Rice Blast.

Yoshio Takahashi, John Hopkins Press, Baltimore, pp. 303–329, 1965, the Rice Blast Disease.

Mathilde A. Causse et. al., Genetics, vol. 138:1251–1274, 1994, Saturated Molecular Map of the Rice Genome Based on an Interspecific Backcross Population.

Shigehisa Kiyosawa, Rice Genetics Newsletter, vol. 1:95–97, 1984, 4. Establishment of Differential Varieties for Pathogenicity Test of Rice Blast Fungus.

Ise, International Rice Research Newsletter, vol. 17:8–9, 1992.

D.J. MacKill et. al., Phytopathology, vol. 82:746–749, 1992, Inheritance of Blasr Resistance in Near–Isogenic Lines of Rice.

T. Inukai et. al., Phytopathology, vol. 84:1278–1283, 1994, Allelism of Blast Resistance Genes in Near–Isogenic Lines of Rice.

Z.H. Yue et. al., Phytopathological, vol. 77:323–326, 1987, Inheritance of Resistance to Blast in Some Traditional and Improved Rice Cultivars.

Z.H. Yu, Theor. Appl. Genet., vol. 81:471–476, 1991, Tagging Genes for Blast Resistance in Rice via Link Age to RFLP Markers.

Zi–Xuan Wang et. al., the Plant Journal, vol. 19:55–64, 1999, the PIB Gene for Rice Blast Resistance Belongs to the Nucleotide Binding and Leucine–Rich Repeat Class PF Plant Disease Resistance Genes.

Steve Whitham et. al., Cell, vol. 78:1101–1115, 1994, the Product of the Tobacco Mosaic Virus Resistance Gene N: Similarity to Toll and the Interleukin–1 Receptor.

National Center for Biotechnology Information General Identifier No. AB013448, Oct. 19, 1999, Wang, Z..X., the PIB Gene for Rice Blast Resistance Belongs to the Nucleotide Binding and Leucine–Rich Repeat Class of Plant Disease Resistance Genes.

Krystyna Rybka et. al., MPMI, vol. 10:517–524, 1997, High Resolution Mapping of the Indica–Derived Rice Blast Resistance Genes II. PI–TA2 and PI–TA and a Consideration of Their Origin.

S. Nakamura et. al., Mol. Gen. Genet., vol. 254:611–620, 1997, Construction of an 800–KB Contig in the Near–Centromeric Region of the Rice Blast Resistance Gene PI–TA2 Using a Highly Representice Rice BAC Library.

Hei Leunget. al., Phytopathology, vol. 78:1227–1233, 1988, Genetic Analysis of Virulence in the Rice Blast Fungus Magnaporthe.

Shigehisa Kiyosawa, Sarrao Journal, vol. 8:53–67, 1976, Pathogenic Variations of *Pyricularia oryzae* and Their Use in Genetic and Breeding Studies.

Desmond Mascarenhas et. al., Plant Molecular, vol. 15:913–920, 1990, Intron–Mediated Enhancement of Heterologous Gene Expression in Maize.

A. Depicker et. al., Journal of Molecular and Applied Genetics, vol. 1:561–574, 1982, Nopaline Synthase: Transcript Mapping and DNA Sequence.

James A. Sweigard et. al., the Plant Cell, vol. 7:1221–1233, 1995, Identification, Cloning and Characterization of PWL2, a Gene for Host Species Specificity in the Rice Blast Fungus.

Desmond G. Higgins et. al., Cabios Communications, vol. 5:151–153, 1989, Fast and Sensitive Multiple Sequence Alignments on a Microcomputer.

Stephen F. Altschul et. al., J. Mol. Biol., vol. 215:403–410, 1990, Basic Local Alignment Search Tool.

Stephen F. Altschul et. al., Nucleic Acids Research, vol. 25:3389–3402, 1997, Gapped Blast and PSI–Blast: a New Generation of Protein Database Search Programs.

Jack K. Okamuro et. al., Biochemistry of Plants, vol. 15:1–82, 1989, Regulation of Plant Gene Expression: General Principles.

Roisin Turner et. al., Mol. Biotechnology, vol. 3:225–236, 1995, the Potential Exploitation of Plant Viral Translational Enhancers in Biotechnology for Increased Gene Expression.

Masao Yamada et. al., Ann. Phytopath. Soc. Japan, vol. 42:216–219, 1976, Proposal of a New Method for Differentiating Races of *Pyricularia oryzae* Cavara in Japan.

J.A. Sweigard et. al., Genetic Maps, 6th Edition, S.J. O'Brien, ed., Cold Spring Harbor Laboratory Press, PP 3.112–3.117, 1993, Genetic Map of the Rice Blast Fungus *Magnaporthe grisea*.

Ericd J. Richards et. al., Cell, Col. 53:127–136, 1988, Isolation of a Higher Eukaryotic Telomere from *Arabidopsis thaliana*.

Staben, C., Fungal. Genet. Newsletter, vol. 36:79–81, 1989, Use of a Bacterial Hygromycin B Resistance Gene as a Dominant Selectable Marker in *Neurospora crassa* Transformation.

D.J. MacKill et. al., Phyopathology, vol. 82:746–749, 1992, Inheritance of Blasr Resistance in Near–Isogenic Lines of Rice.

Long Mao et. al., Genome Research, vol. 10:982–900, 2000, Rice Transposable Elements: a Survey of 73,000 Sequence–Tagged –Connectors.

Toshio Murashige et. al., Physoil. Plant, vol. 15:473–497, 1962, a Revised Medium for Rapid Growth and Bio Assays with Tobacco Tissue Cultures.

Richard A. Jefferson, Plant Mol. Bio. Rep., vol. 5:387–405, 1987, Assaying Chimericf GNES in Plants: the GUS Gene Fusion System.

Jonathan D.G. Jones et. al., the Embro Journal, vol. 4:2411–2418, 1985, High Level Expression of Introduced Chimaeric Genes in Regenerated Transformed Plants.

* cited by examiner

```
                                                                      60
     1  MLFYS.LFFF HTVAISAFTN IGTFSHPVYD YNPIPNHIHG DLKRRAYIER YSQCSDSQAS
O-137   ---------- ---------- ------Y--I ---------- ---------- ----------
G-213   ----FI-Y-- ---------- ---------- ---------- --------P- ---N--D---
Ina 72.1 ---L--L--- ---------- ---------- ---------- ---------- ----------
Ina 72.2 ---L--L--- ---------- ---------- ---------- ---------- ----------
G-198   ---D--.--- ---------- ----C----- ---------- ---------- ----------
GUY11   ---------- ---------- ---------- ---------- ---------- ----------

120
    61  EIRAALKSCA ELASWGYHAV KNDNRLFRLI FKTDSTDIQN WVQKNFNEIY KECNRDADEI
O-137   ---------- -------A-- ------E--- E--------- ---N------ ----------
G-213   ---------- ---------- ---------- ---------- --------H- ----------
Ina 72.1 ---------- ---------- -------S-- ------N-K- ---N------ ----------
Ina 72.2 ---------- ---------- ------SN-- ------N-K- ---N------ ----------
G-198   ---------- ---------- ------SN-- ------N-K- ---N------ ----------
GUY11   ---------- ---------- ------SN-- ------N-K- ---N------ ----------

180
   121  SLTCHDKNVY TCVREGVHNL AYALINEKEI VICPPFFNNP VNSREITAGN QDTVILHEMV
O-137   -S----TS-- ------L--- G--KMY--QV ----H--DH- --------Q- ---------L
G-213   ---------- ---------- ---------- ---------- ---------- ----I-----
Ina 72.1 ---------- ------E--- ---------- ---------- ---------- ----I-----
Ina 72.2 ---------- ------E--- ---------- ---------- ---------- ----I-----
G-198   ---------- -------Q-- ---------- ---------- ---------- ----I-----
GUY11   ---------- ---------- ---------- ---------- ---------- ----------

224
   181  HIILKEWKDY GYEWDGIHKL DSTESIKNPD SYAIFAQCAR YKYC
O-137   --N------- ---------- ------T--- ---------- ----
G-213   ---------- ---------- ---------- ---------- ----
Ina 72.1 ----C----- ---N------ ---------- ---------- ----
Ina 72.2 ----C----- ---------- ---------- ---------- ----
G-198   ----C----- ---------- ---------- ---------- ----
GUY11   ---------- ---------- ---------- ---------- ----
```

FIG. 1

MODIFICATION OF PI-TA GENE CONFERRING FUNGAL DISEASE RESISTANCE TO PLANTS

This application claims the benefit of U.S. Provisional Application No. 60/248,335, filed Nov. 14, 2000, the entire contents of which are herein incorporated by reference.

FIELD OF THE INVENTION

This invention relates to the preparation and use of an isolated nucleic acid fragment in order to confer a resistance gene mediated defense response in plants against a fungus comprising in its genome virulent and/or avirulent AVR-Pita alleles. Chimeric genes incorporating such fragments or functionally equivalent subfragments thereof and suitable regulatory sequences can be used to create transgenic plants which can produce a resistance gene mediated defense response against a fungus comprising in its genome virulent and/or avirulent AVR-Pita alleles.

BACKGROUND OF THE INVENTION

Plants can be damaged by a wide variety of pathogenic organisms including viruses, bacteria, fungi and nematodes. The invasion of a plant by a potential pathogen can result in a range of outcomes: the pathogen can successfully proliferate in the host, causing associated disease symptoms, or its growth can be halted by the host defenses. In some plant-pathogen interactions, the visible hallmark of an active defense response is the so-called hypersensitive response (HR). The HR involves rapid necrosis of cells near the site of the infection and may include the formation of a visible brown fleck or lesion. Pathogens which elicit an HR on a given host are said to be avirulent (AVR) on that host, the host is said to be resistant, and the plant-pathogen interaction is said to be incompatible. Strains which proliferate and cause disease on a particular host are said to be virulent, in this case the host is said to be susceptible, and the plant-pathogen interaction is said to be compatible.

Genetic analysis has been used to help elucidate the genetic basis of plant-pathogen recognition for those cases in which a series of strains (races) of a particular fungal or bacterial pathogen are either virulent or avirulent on a series of cultivars of a particular host species. In many such cases, genetic analysis of both the host and the pathogen revealed that many avirulent fungal and bacterial strains differ from virulent ones by the possession of one or more avirulence ("avr" or "AVR") genes that have corresponding "resistance" (R) genes in the host.

This avirulence gene-resistance gene model is termed the "gene-for-gene" model (Crute et al. (1985) pp 197–309 in: Mechanisms of Resistance of Plant Disease. R. S. S. Fraser, ed.; Ellingboe, (1981) *Annu. Rev. Phytopathol.* 19:125–143; Flor, (1971) *Annu. Rev. Phythopathol.* 9:275–296). According to a simple formulation of this model, plant resistance genes encode specific receptors for molecular signals generated by avr genes. Signal transduction pathway(s) then carry the signal to a set of target genes that initiate the host defenses. Despite this simple predictive model, the molecular basis of the avr-resistance gene interaction is still unknown.

The first R-gene cloned was the Hm1 gene from corn (*Zea mays*), which confers resistance to specific races of the fungal pathogen *Cochliobolus carbonum* (Johal et al., 1992, *Science* 258:985–987). Hm1 encodes a reductase that detoxifies a toxin produced by the pathogen. Next to be cloned was the Pto gene from tomato (*Lycopersicon pimpinellifollium*) (Martin et al., 1993, *Science* 262:1432–1436; U.S. Pat. No. 5,648,599). Pto encodes a serine-threonine protein kinase that confers resistance in tomato to strains of the bacterial pathogen *Pseudomonas syringae* pv. tomato that express the avrPto avirulence gene. Taking center stage now are R-genes that encode proteins containing leucine-rich-repeats (LRRs) (Jones and Jones, 1997, *Adv. Bot Res. Incorp. Adv. Plant Pathol.* 24:89–167). Two classes of membrane anchored proteins with extracellular LRRs have been identified. One subclass includes R-gene products that lack a cytoplasmic serine/threonine kinase domain such as the tomato Cf-9 gene for resistance to the fungus *Cladosporium fulvum* (Jones et al., 1994, *Science* 266:789–793, WO 95/18230), and the other subclass includes an R-gene product with a cytoplasmic serine/threonine kinase domain, the rice Xa-21 gene for resistance to the bacterial pathogen *Xanthomonas oryzae* (Song et al., 1995, *Science* 270:1804–1806; U.S. Pat. No. 5,859,339). The largest class of R-genes includes those encoding proteins with cytoplasmic LRRs such as the Arabidopsis R-genes RPS2 (Bent et al., 1994, *Science* 265:1856–1860; Mindrinos et al., 1994, *Cell* 78:1089–1099) and RPM1 (Grant et al., 1995, *Science* 269:843–846). These R-proteins also possess a putative nucleotide binding site (NBS), and either a leucine zipper (LZ) motif or a sequence homologous to the Toll/Interleukin-1 receptor (TIR). Table 1 has been reproduced in part from Baker et al. (1997, *Science* 276:726–733) as a concise summary of classes of R-genes cloned to date and examples of cloned genes within each class.

TABLE 1

Isolated plant resistance genes[1]

| Class | R gene | Plant | Pathogen | Structure |
|---|---|---|---|---|
| 1 | RPS2 | Arabidopsis | *Pseudomonas syringae* pv. Tomato | LZ-NBS-LRR |
|  | RPM1 | Arabidopsis | *P. syringae* pv. Maculicola | LZ-NBS-LRR |
|  | Prf | Tomato | *P. syringae* pv. Tomato | LZ-NBS-LRR |
|  | N | Tobacco | Tobacco mosaic virus | TIR-NBS-LRR |
|  | L[6] | Flax | *Melampsora lini* | TIR-NBS-LRR |
|  | M | Flax | *M. lini* | TIR-NBS-LRR |
|  | RPP5 | Arabidopsis | *Peronospora parasitica* | TIR-NBS-LRR |
|  | I$_2$ | Tomato | *Fusarium oxysporum* | NBS-LRR |
| 2 | Pto | Tomato | *P. syringae* pv. Tomato | Protein kinase |
| 3 | Cf-9 | Tomato | *Cladosporium fulvum* | LRR-TM |
|  | Cf-2 | Tomato | *C. fulvum* | LRR-TM |
|  | HS1$^{pro-1}$ | Sugar beet | *Heterodera schachtii* | LRR-TM |
| 4 | Xa21 | Rice | *Xanthomonas oryzae* pv. *Oryzae* | LRR, protein kinase |
| 5 | Hm1 | Maize | *Cochilobolus carbonum*, race 1 | Toxin reductase |

[1]This Table has been reproduced in part from Baker et al. (1997, Science 276:726–733). References for each of the listed R-genes can be found in this review article.

Nucleotide binding sites (NBS) are found in many families of proteins that are critical for fundamental eukaryotic cellular functions such as cell growth, differentiation, cytoskeletal organization, vesicle transport, and defense. Key examples include the RAS group, adenosine triphosphatases, elongation factors, and heterotrimeric GTP binding proteins called G-proteins (Saraste et al., 1990, *Trends in Biochem. Science* 15:430). These proteins have in common the ability to bind ATP or GTP (Traut, 1994, *Eur. J. Biochem.* 229:9–19).

It has long been hypothesized that the rice blast system represented a classical gene-for-gene system as defined by H. H. Flor (Flor, 1971, *Annu. Rev. Phytopathol.* 19:125–143). Genetic analyses needed to identify AVR-genes in the rice blast pathogen, *Magnaporthe grisea*, has been hampered by the low fertility that typifies *M. grisea* field isolates that infect rice. Genetic crosses between poorly fertile *M. grisea* rice pathogens and highly fertile *M. grisea* pathogens of other grasses (such as weeping lovegrass, *Eragrostis curvula*, and finger millet, *Eleusine coracana*) have provided laboratory strains of the fungus with the level of sexual fertility required for identifying AVR-genes (Valent et al., 1991*, Genetics* 87–101). Rare fertile rice pathogens have since allowed demonstration of a one-to-one genetic or functional correspondence between blast fungus AVR-genes and particular rice R-genes (Silue et al., 1992*, Phytopathology* 82:577–580).

Interest in the rice blast pathosystem is keen because rice blast disease, caused world-wide by the fungal pathogen *Magnaporthe grisea* (Hebert) Barr (anamorph *Pyricularia grisea* Sacc.), continues as the most explosive and potentially damaging disease of the rice crop despite decades of research towards its control. Manipulation of blast resistance genes remains one of the primary targets in all rice breeding programs, as fungal populations evolve to defeat deployed resistance strategies (See The Rice Blast Disease, 1994, ed. Zeigler, Leong and Teng, CAB International, Wallingford).

Commercial fungicide usage to supplement genetic control strategies began around 1915 when rice farmers used inorganic copper-based fungicides (Chapter 29 in The Rice Blast Disease, 1994, ed. Zeigler, Leong and Teng, CAB International, Wallingford). The fungicides used to control blast disease have changed through time, with some compounds, such as the organomercurials used in the 1950s, causing major environmental damage. The control of rice blast with fungicides currently represents a cost of more than $500 million per year to farmers. This expense for blast control is the largest segment of the world rice fungicide market, which totaled $752 million in 1998 (Wood Mackenzie). Expectations are that the disease problems will intensify as the world rice requirements increase by an estimated 1.7% annually between 1990 and 2025 (See The Rice Blast Disease, 1994, ed. Zeigler, Leong and Teng, CAB International, Wallingford). This estimated need for an additional 13 million tons of rough rice per year to feed the growing population must come from intensification of production on decreasing available land. Rice blast disease is favored by agronomic production practices aimed at high yields, and thus the disease will continue, and most likely increase, as a constraint to rice crop yields unless durable genetic resistance against rice blast disease can be engineered into rice. This invention represents an advance towards the long term goal of engineering durable genetic resistance to rice blast by generating novel Pi-ta alleles that have different specificities as regards the spectrum of AVR-Pita gene products they recognize. The fungus *M. grisea* has a large host range including species of different tribes within the grass family, Triticeae (e.g., wheat), Oryzeae (e.g., rice), Clorideae (e.g., finger millet), Paniceae (e.g., pearl millet), Andropogoneae (e.g., sorghum) and Maydeae (e.g., maize). Molecular analyses have now defined 8 host species-specific subpopulations of *M. grisea*, each with a restricted set of host species specificities (Reviewed by Valent, 1997, The Mycota V, Plant Relationships, Carroll/Tudzynski, eds., Springer-Verlag Berlin Heidelberg pp 37–54). Table 2 gives a current view of pathogen subpopulations according to mitochondrial DNA (mtDNA) type. This view is strongly supported by separate analyses of ribosomal DNA (rDNA) polymorphisms (including both Restriction Fragment Length Polymorphism (RFLP) and Internal Transcribed Spacer (ITS) sequences) and of polymorphisms in both repetitive DNAs and single copy sequences.

The pathogens of rice, wheat, finger millet, barley and corn (mtDNA types Ia-e) appear closely related, while pathogens of Digitaria spp. and Pennisetum spp. (mtDNA types II–IV) are highly divergent from the previous groups and from each other. However, *M. grisea* strains throughout this broad host range can cause significant crop damage. This pathogen has been shown to be the main cause of yield loss of finger millet (*Eleusine coracana*) in Africa, while infections in wheat (*Triticum aestivum*; Urashima et al., 1993*, Plant Disease* 77:1211–1216) and pearl millet (*Pennisetum glaucum*; Hanna et al., 1989*, J. Heredity* 80:145–147), although less widespread, can be severe under humid weather conditions. The disease has been documented on barley and corn (See refs. In Urashima et al., 1993*, Plant Disease* 77:1211–1216).

TABLE 2

Host Specificities Within *Magnaporthe grisea*

| Subpopulation[1] | Defining Host Species[2] | Crops at Risk |
|---|---|---|
| Ia | *Oryza sativa* | Rice, Barley, Corn |
| Ib | *Triticum aestivum* | Wheat, Barley |
| Ie | Eleusine spp. | Finger Millet |
| Ic | Eleusine spp. | Finger Millet |
| IIa | Digitaria spp. | |
| IIb | Digitaria spp. | |
| III | Pennisetum spp. | Pearl Millet |
| IV | Pennisetum spp. | |

[1]Designated by mitochondrial-DNA haplotype.
[2]Pathogenicity to the "Defining Host Species" appears conserved within the subpopulation. Some hosts, such as barley, are infected by members of two or more subpopulations.

Knowledge of pathogenicity and host specificity for plant pathogenic fungi is not as advanced as for bacterial and viral pathogens, an d likewise, less is known about the molecular basis of resistance in cereal crop plants than in dicot crops or in dicot model systems such as Arabidopsis (Baker et al., 1997*, Science* 276:726–733). Sasaki reported the first results on the inheritance of resistance to rice blast disease from studies begun in Japan in 1917 (Sasaki, 1922*, Japanese Genetics*, Japan 1, 81–85).

Since this time, over 30 R-genes have been defined through extensive genetic analysis worldwide, and many of these blast resistance genes have been mapped to rice chromosomes (See Refs. In Takahashi, 1965, The Rice Blast Disease, Johns Hopkins Press, Baltimore, 303–329; Causse et al., 1994*, Genetics* 138:1251–1274). These R-genes include 20 major resistance genes and 10 putative quantitative trait loci (QTLs). Kiyosawa has described 13 major resistance genes with 9 of these genes found as multiple alleles at 3 loci; 5 at the Pi-k locus on chromosome 11, 2 at the Pi-z locus on chromosome 6 and 2 at the Pi-ta locus on chromosome 12 (Kiyosawa, 1984*, Rice Genetics Newsletter* 1:95–97). Recent studies in Japan (Ise, 1992*, International Rice Research Newsletter* 17:8–9) and at the International Rice Research Instiitute (IRRI) (Mackill et al., 1992*, Phytopathology* 82:746–749) have produced near isogenic rice lines (NILs) for use as "differential" rice varieties for determining which resistance genes are effective in controlling individual strains of the fungus. The IRRI NILs, which provide indica differentials for the blast fungus populations in tropical regions, have been analyzed for genetic relationships between their resistance genes and those present in Kiyosawa Differentials (Inukai et al., 1994*, Phytopathology* 84:1278–1283).

Molecular markers (or "tags") tightly linked to R-genes have utility for efficient introgression and manipulation of those R-genes in breeding programs. By comparing genotypic patterns of near-isogenic lines, their donors, and their recurrent parents, Yu et al. (1987, *Phytopathology* 77:323–326) were able to identify five restriction fragment length polymorphic (RFLP) markers linked to three blast resistance genes and to map them to rice chromosomes using segregating populations. RFLP markers linked to the R-genes have been reported (Yu et al., 1991, *Theor Appl Genet* 81:471–476). Molecular cloning of agronomically important R-genes represents a further advance to the ability of researchers to combine R-genes with other input and output traits in key crop varieties.

In the course of the above mentioned investigations on the inheritance of resistance, Sasaki discovered physiological races of the rice blast pathogen by observing that different field isolates of the blast fungus vary in their ability to cause disease on different varieties of rice (Sasaki, 1922, *Journal of Plant Protection* 9:631–644; Sasaki, 1923, *Journal of Plant Protection* 10:1–10). Instability, or "breaking down" under field conditions, of major R-gene resistance to the rice blast fungus has resulted in identification of numerous races, or pathotypes, defined according to virulence spectra on differential rice varieties (Chapters 13 and 16 in The Rice Blast Disease, 1994, ed. Zeigler, Leong and Teng, CAB International, Wallingford). Pathogen populations are dynamic in response to deployment of a new resistance gene, sometimes resulting in new races that overcome the resistance gene within one or two years after deployment in the field.

Accordingly, incorporation of diseases resistance (R) genes into crop plants has not achieved durable resistance to highly variable fungal pathogens such as *Magnaporthe grisea* (Hebert) Barr, the causal agent of the devastating rice blast disease worldwide. (Rossman et al., Commonwealth Mycological Institute, Kew, Surrey, Second Edition, 1985; Rice Blast Disease, Zeigler et al., eds., CAB International, Wallingford, Oxon OX108DE, UK (1994)). In other words, R-gene utility in controlling rice blast disease has been limited by the inherent field variability of the pathogen.

There are a number of virulent AVR-Pita alleles in different strains of *M. grisea* for which no corresponding R-gene variants have been identified in rice that recognize these alleles. No one heretofore has been able to engineer an R-gene to recognize such alleles. Clearly, an ability to do so would provide a valuable tool to control currently virulent strains of the rice blast fungus and other pathogens.

Clearly, researchers have not adequately succeeded in this regard.

Applicants' assignee's copending patent application which was filed on Jun. 21, 1999 and having application Ser. No. 09/336,946 (PCT Publication No. WO 00/08162, which was published on Feb. 17, 2000), describes a Pi-ta gene conferring disease resistance. It does not address the need to modify R-genes to increase their utility by altering their specificity with respect to the AVR-Pita alleles which it can recognize in different strains of a fungus.

Wang et al. (1999) *Plant J* 19:55–64 describe another rice blast resistance gene, Pib, different from Pi-ta.

WO 00/34479, which published on Jun. 15, 2000, describes nucleic acid fragments which encode a different disease resistance protein that confers resistance to *M. grisea*.

U.S. Pat. No. 5,648,599, issued to Tanksley and Martin on Jul. 15, 1997, describes an isolated gene fragment from tomato which encodes the Pto serine/threonine kinase, conferring disease resistance to plants by responding to an avirulence gene in a bacterial plant pathogen.

WO 95/28423, which published on Oct. 26, 1995, describes resistance due to the *Pseudomonas syringae* RPS2 gene family, primers, probes and detection methods. This published international application includes broad claims to genes encoding proteins with particular $NH_2$-terminal motifs, NBS motifs and leucine rich repeats for protecting plants against pathogens. There are some unique features of the Pi-ta protein. The Pi-ta gene product has a unique amino terminus, lacking either the potential leucine zipper motif of the RPS2 gene-product subfamily (Bent et al., 1994, *Science* 265:1856–1860; Mindrinos et al., 1994, *Cell* 78:1089–1099) or the Toll/Interleukin-1 receptor homology encoded by the N gene subfamily (Whitman et al., 1994, *Cell* 78:1101–1115). Most importantly, the carboxy terminal portion of the Pi-ta gene product is leucine rich, but it does not fit the consensus sequences for leucine-rich repeats reported for R-gene products (Jones and Jones, 1997, *Adv. Bot Res. Incorp. Adv. Plant Pathol.* 24:89–167).

U.S. Pat. No. 5,571,706, issued to Baker et al. on Nov. 5, 1996, covers plant virus resistance conferred by the N gene.

U.S. Pat. No. 5,859,351, issued to Staskawicz et al. on Jan. 12, 1999, describes the PRF protein and nucleic acid sequence, which is involved in disease resistance in tomato.

U.S. Pat. No. 5,859,339, issued to Ronald et al. on Jan. 12, 1999, describes the first resistance gene cloned from rice, Xa-21, which encodes an integral membrane protein with both LRR and serine/threonine kinase domains, and confers resistance in rice to bacterial blight.

WO 91/15585 which published on Oct. 17, 1991 and U.S. Pat. No. 5,866,776 issued to de Wit et al. on Feb. 2, 1999 describe a method for the protection of plants against pathogens using a combination of a pathogen avirulence gene and a corresponding plant resistance gene.

U.S. Pat. No. 5,674,993 ('993 patent), issued to Kawasaki et al. on Oct. 7, 1997, describes nucleic acid markers that co-segregate with the rice blast resistance genes Pi-b, Pi-ta and Pi-ta$^2$ and the suggestion that rice blast resistance genes could be isolated and cloned by using these nucleic acid markers. However, no nucleotide sequences are provided for any rice blast resistance genes in the '993 patent. It should be noted that a putative sequence for the Pi-b rice blast resistance gene is now available in Genbank (accession number AB013448).

In addition, Kawasaki et al. have also published two papers. The first paper, Rybka et al., *MPMI*, 10(4):517–524 (1997), is entitled "High Resolution Mapping of the Indica-Derived Rice Blast Resistance Genes. II. Pi-ta$^2$ and Pi-ta and a Consideration of Their Origin." The sequence for the RAPD primer that is set forth at the top of column 2 on page 519 is not the same as the RAPD primer set forth in SEQ ID NO:2 in the '993 patent. It is not clear which sequence is correct. Notwithstanding this, it is clear that this paper does not set forth any nucleotide sequences for any rice blast genes. The second paper is Nakamura et al., *Mol. Gen. Genet.* 254:611–62 (1997). This paper describes the construction of an 800-kb contig in the near-centromeric region of the rice blast resistance gene Pi-ta$^2$ using a rice BAC library. Again, no nucleotide sequence for any rice blast genes is disclosed.

Thus, it is believed that no one heretofore has addressed the need to modify R-genes to increase their utility by broadening their specificity with respect to the AVR-Pita alleles. The broadened specificity enables the modified R-gene to recognize different fungal strains.

SUMMARY OF THE INVENTION

This invention relates to an isolated nucleic acid fragment comprising a nucleic acid sequence or subsequence thereof encoding an altered Pi-ta resistance polypeptide wherein the polypeptide has a single amino acid alteration at position 918 which confers a resistance gene mediated defense response against a fungus comprising in its genome virulent and/or avirulent AVR-Pita alleles.

In another aspect, this invention concerns alterations at position 918 which are selected from the group consisting of M, C, I, R, K, N, L and Q.

In still another aspect, this invention concerns chimeric genes comprising the nucleic acid fragment of the invention.

Also of interest are plants comprising in their genome the chimeric genes described herein as well as seeds obtained from such plants.

In an even further aspect, this invention concerns a method of conferring a resistance gene mediated defense response in plants against a fungus comprising in its genome virulent and/or avirulent AVR-Pita alleles in plants which comprises:
 (a) transforming a plant with a chimeric gene of the invention; and
 (b) selecting transformed plants of step (a) which are resistant to a fungus comprising in it genome virulent and/or avirulent AVR-Pita alleles.

Biological Deposit

The fungal strain O-137 (collected in 1985 at the China National Rice Research Institute in Hangzhou) has been deposited with the American Type Culture Collection (ATCC), 10801 University Boulevard, Manassas, Va. 20110-2209, and bears the following designation, accession number and date of deposit. Fungal strain G-213, a pathogen isolated from *Digitaria smutsii* in Japan, was obtained from the collection of Jean Loup Notteghem, Laboratoire de phytopathologie, Institut de Recherches Agronomiques Tropicales et des Cultures Vivrieres, Centre de Cooperation Internationale en Recherche Agronomique pour le Developpement (CIRAD), BP 5035, 34032 Montpellier Cedex 1, France, and is available under the name JP34. Rice pathogen strain G-198, also obtained from Jean Loup Notteghem, was originally isolated from barley in Thailand. Rice pathogen strain GUY11, also obtained from Jean Loup Notteghem, is described in Leung et al. (1988) *Phytopathology* 78, 1227–1233. Rice pathogen strain Ina 72 is described in Kiyosawa (1976) *SABRAO Journal* 8:53–67. All strains have been deposited with the ATCC.

Plasmid pCB2022 which contains sequences of Pi-ta promoter, Pi-ta cDNA, linker sequence and In2-1 terminator sequence described in Example 6 has likewise been deposited with the ATCC.

| Designation | Material | Accession Number | Date of Deposit |
| --- | --- | --- | --- |
| O-137 | *M. grisea* | ATCC 74457 | Aug. 3, 1998 |
| G-213 | *M. grisea* | PTA-191 | Jun. 8, 1999 |
| G-198 | *M. grisea* | PTA-190 | Jun. 8, 1999 |
| GUY 11 | *M. grisea* | PTA-192 | Jun. 8, 1999 |
| Ina 72 | *M. grisea* | PTA-2606 | Oct. 18, 2000 |
| pCB2022 | Plasmid | PTA-2631 | Oct. 25, 2000 |

BRIEF DESCRIPTION OF THE SEQUENCE LISTINGS AND FIGURES

SEQ ID NO:1 sets forth the sequence of plasmid pCB980 which is a 4119 bp plasmid containing sequences of pBluescript SK+ (nucleotides 1–676, 1880–4119), AVR-Pita promoter (nucleotides 677–1157) and AVR-Pita cDNA (nucleotides 1158–1829) from *M. grisea* strain O-137.

SEQ ID NO:2 is the 672 nucleotide sequence of an AVR-Pita cDNA from *M. grisea* strain O-137.

SEQ ID NO:3 is the predicted amino acid sequence of the protein encoded by the AVR-Pita cDNA sequence set forth in SEQ ID NO:2.

SEQ ID NO:4 is the 788 nucleotide sequence of an AVR-Pita cDNA from *M. grisea* strain G-198.

SEQ ID NO:5 is the predicted amino acid sequence of the protein encoded by the AVR-Pita cDNA set forth in SEQ ID NO:4.

SEQ ID NO:6 is a predicted 672 nucleotide sequence of an AVR-Pita cDNA from *M. grisea* strain GUY 11 based on genomic sequence set forth in SEQ ID NO:59.

SEQ ID NO:7 is the predicted amino acid sequence of the protein encoded by the AVR-Pita cDNA set forth in SEQ ID NO:6.

SEQ ID NO:8 is the 884 nucleotide sequence of an AVR-Pita genomic clone from *M. grisea* strain Ina 72.

SEQ ID NO:9 is a predicted 675 nucleotide sequence of an AVR-Pita cDNA from *M. grisea* strain Ina 72 based on genomic sequence set forth in SEQ ID NO:8.

SEQ ID NO:10 is the predicted amino acid sequence of the protein (Ina 72.1) encoded by the predicted AVR-Pita cDNA sequence set forth in SEQ ID NO:9.

SEQ ID NO:11 is the 884 nucleotide sequence of a second AVR-Pita genomic clone from *M. grisea* strain Ina 72.

SEQ ID NO:12 is a predicted 675 nucleotide sequence of an AVR-Pita cDNA from *M. grisea* strain Ina 72 based on genomic sequence set forth in SEQ ID NO:11.

SEQ ID NO:13 is the predicted amino acid sequence of the protein (Ina 72.2) encoded by the predicted AVR-Pita cDNA sequence set forth in SEQ ID NO:12.

SEQ ID NO:14 is the 884 nucleotide sequence of an AVR-Pita genomic clone from *M. grisea* strain G-213.

SEQ ID NO:15 is a predicted 675 nucleotide sequence of an AVR-Pita cDNA from *M. grisea* strain G-213 based on genomic sequence set forth in SEQ ID NO:14.

SEQ ID NO:16 is the predicted amino acid sequence of the protein encoded by the predicted AVR-Pita cDNA sequence set forth in SEQ ID NO:15.

SEQ ID NOS:17 and 18 are PCR primers used to amplify AVR-Pita cDNA and genomic DNA from strain O-137, and an AVR-Pita genomic nucleic acid fragment from strains G-198 and GUY11.

SEQ ID NOS:19 and 20 are PCR primers used to amplify a functional AVR-Pita promoter fragment from strain O-137.

SEQ ID NO:21 is a PCR primer used along with SEQ ID NO:18 to amplify AVR-Pita genomic nucleic acid fragments from strain Ina 72.

SEQ ID NOS:22 and 23 are PCR primers used to amplify an AVR-Pita genomic nucleic acid fragment from strain G-213.

SEQ ID NOS:24 and 25 are PCR primers used to amplify an AVR-Pita nucleic acid fragment in the process of constructing pAVR3.

SEQ ID NOS:26 and 27 are PCR primers used to amplify AVR-Pita$_{176}$, an AVR-Pita nucleic acid fragment that directly encodes the putative mature protease.

SEQ ID NOS:28 and 29 are PCR primers used to amplify AVR-Pita cDNA from strain G-198.

SEQ ID NOS:30 and 31 are PCR primers used to amplify a partial Pi-ta cDNA.

SEQ ID NO:32 is a PCR primer used along with SEQ ID NO:30 to amplify a susceptible Pi-ta nucleic acid fragment from susceptible C101A51 rice.

SEQ ID NOS:33–51 are PCR primers used to modify Pi-ta coding sequence, resulting in an array of plasmids comprising nucleic acid fragments that encode different Pi-ta proteins with all 20 amino acids represented at position 918.

SEQ ID NOS:52 and 53 are PCR primers used to amplify the Pi-ta leucine rich domain (LRD).

SEQ ID NOS:54 and 55 are PCR primers used to amplify the In2-1 terminator sequence.

SEQ ID NO:56 is the 5757 nucleotide sequence of the genomic clone of the Pi-ta gene from Oryza sativa variety Yashiro-mochi.

SEQ ID NO:57 is the 5222 nucleotide sequence of an EcoRI-Hind III fragment that contains 2425 bp of the native Pi-ta promoter (nucleotides 1 to 2425) and Pi-ta cDNA (nucleotides 2426–5212) from rice variety Yashiro-mochi.

SEQ ID NO:58 is the predicted Pi-ta protein sequence encoded by the Pi-ta nucleotide sequences set forth in SEQ ID NOS:56 and 57.

SEQ ID NO:59 is the 881 nucleotide sequence of an AVR-Pita genomic clone from *M. grisea* strain GUY11.

SEQ ID NO:60 sets forth the sequence of the insert in plasmid pCB2022 which contains sequences of Pi-ta promoter (nucleotides 1–2425), Pi-ta cDNA (nucleotides 2426–5212), linker sequence (nucleotides 5213–5241) and In2-1 terminator sequence (nucleotides 5242–5690).

FIG. 1. Comparison of the deduced amino acid sequences encoded by avirulent and virulent AVR-Pita nucleic acid fragments. The AVR-Pita nucleic acid fragments from avirulent strains O-137 (SEQ ID NO:3) and G-213 (SEQ ID NO:16), and the first sequence from strain Ina 72 (Ina 72.1; SEQ ID NO:10) have been shown to confer avirulence (Example 5). The nucleic acid fragment encoding the second Ina 72 sequence (Ina 72.2; SEQ ID NO:13) and the fragments from virulent strains G-198 (SEQ ID NO:5) and Guy11 (SEQ ID NO:7) do not confer avirulence (Example 5). Only differences from the deduced amino acid sequence of AVR-Pita from strain O-137 (SEQ ID NO:3) are indicated. Identical amino acids are indicated by a dash (-), whereas a gap that is introduced to maximize alignment is indicated by a dot (.). The underlined amino acids indicate the putative protease motif.

FIG. 2. Diagram of constructs in plasmids pCB1947, pML63 and pCB1926.

A. pCB1947 contains a construct of the AVR-Pita isolated nucleic acid fragment (formerly called AVR2-YAMO) engineered to encode directly the putative mature protease for the transient expression experiments. This processed form of the isolated nucleic acid fragment, designated AVR-Pita$_{176}$, encodes a polypeptide comprised of amino acids 48 to 223 as set forth in SEQ ID NO:6. An initiation methionine was added to the construct through the NcoI site used in the cloning process. The AVR-Pita coding sequence was first amplified by PCR using primers YL30 (SEQ ID NO:26) containing an in-frame NcoI site and YL37 (SEQ ID NO:27) containing a KpnI site, and cloned into the NcoI-KpnI site of pML142, resulting in vector pCB1947. The maize Adh1-6 intron inserted downstream of the 35S promoter results in enhanced expression in monocots. This intron is described in Mascarenhas et al. (1990) *Plant Mol Biol.* 15:913–920.

B. pML63 contains the uidA gene (which encodes the GUS enzyme) operably linked to the CaMV35S promoter and 3' NOS sequence. pML63 is modified from pMH40 to produce a minimal 3' NOS terminator fragment. pMH 40 is described in WO 98/16650 which published on Apr. 23, 1998, the disclosure of which is hereby incorporated by reference. Using standard techniques familiar to those skilled in the art, the 770 base pair terminator sequence contained in pMH40 was replaced with a new 3' NOS terminator sequence comprising nucleotides 1277 to 1556 of the sequence published by Depicker et al. (1982*, J. Appl. Genet.* 1:561–574).

C. pCB1926 contains the Pi-ta cDNA construct that was created by first amplifying a 2.1 kb partial Pi-ta cDNA nucleic acid fragment from first strand cDNA using primers F12-1 (SEQ ID NO:31) and GB67 (SEQ ID NO:30). A synthetic full-length cDNA was generated by incorporating a 706 bp NcoI-BamHI fragment containing the 5' end of the genomic Pi-ta gene from pCB1649, resulting in plasmid pCB1906. A 3.1 kb EcoRI fragment from pCB1649 containing 2425 bp of the native Pi-ta promoter sequences (pPi-ta) and 736 bp of the 5' Pi-ta coding sequence was then inserted into the EcoRI sites of pCB1906 to replace the 736 bp 5' end of the synthetic cDNA nucleic acid fragment, producing pCB1926.

FIG. 3. DNA Genomic Blot Analysis of AVR-Pita Copy Number. *M. grisea* genomic DNA from the indicated strains was isolated as described previously (Sweigard et al., 1995*, The Plant Cell* 7:1221–1233), digested with Eco RI, electrophoretically fractionated through an agarose gel, blotted onto a filter, and probed with an AVR-Pita fragment using standard molecular biology protocols (Sambrook). Since there is no Eco RI site in the AVR-Pita gene, the number of bands per lane indicates the number of AVR-Pita genes present in that particular *M. grisea* strain. For example, the leftmost lane shows the result for *M. grisea* strain G-198 which shows two bands, indicating that G-198 has two AVR-Pita genes. The short horizontal lines along the left border of the figure indicate the location of DNA size markers from a HindIII digest of λ DNA of sizes from top to bottom of 23.1 kb, 9.4 kb, 6.6 kb, 4.4 kb, 2.3, and 2.0 kb.

DESCRIPTION OF THE INVENTION

In the context of this disclosure, a number of terms shall be utilized.

The term "disease resistance gene" means a gene encoding a polypeptide capable of triggering a defense response in a plant cell or plant tissue. The terms "disease resistance gene", "resistance (R) gene" and "R" gene are used interchangeably herein. The resistance that results from a defense response can take several forms. For example, in some genetic backgrounds resistance may take the form of no visible symptoms on inoculated plant tissue, and in others resistance may include small brown spots from which the fungus does not sporulate and does not reinitiate infection. In both cases, the fungal pathogen does not complete its life cycle and disease development is stopped. In some cases disease resistance may take the form of smaller-sized lesions that do not produce the quantity of fungal spores typical of the full disease.

A "defense response" is a specific defensive reaction produced by a host, e.g., a plant, to combat the presence of an infectious agent or pathogen.

A "Pi-ta resistance gene" is a disease resistance gene encoding a Pi-ta-resistance polypeptide capable of triggering a defense response in a plant cell or plant tissue against a fungal pathogen such as *Magnaporthe grisea.*

The term "Pi-ta resistance gene mediated defense response" means a defense response due to the production of the polypeptide encoded by the Pi-ta resistance gene and elicited by the presence of a fungal pathogen. The term "resistance gene mediated defense response" means a defense response due to the production of a polypeptide encoded by a resistance gene and elicited by the presence of a fungal pathogen or a fungal pathogen elicitor.

A "fungal pathogen elicitor" is a pathogen signal molecule that is directly or indirectly recognized by a resistance gene product.

A "virulent AVR-Pita allele" is a variant of the AVR-Pita gene whose gene product normally does not elicit a Pi-ta resistance gene-mediated defense response in rice that expresses the functional Pi-ta resistance protein (A918 described herein; SEQ ID NO:58) such as Yashiro-mochi. The avr-pita gene from M. grisea strain G-198 described herein is an example of a virulent AVR-Pita allele.

An "avirulent AVR-Pita allele" is a variant of the AVR-Pita gene whose gene product normally elicits a Pi-ta resistance gene-mediated defense response in rice that expresses the functional Pi-ta resistance protein (A918 described herein; SEQ ID NO:58) such as Yashiro-mochi. The AVR-Pita gene from *M. grisea* strain O-137 described herein is an example of an avirulent AVR-Pita allele.

An "AVR-Pita isolated nucleic acid fragment" is a nucleic acid fragment isolated from a pathogen wherein the nucleic acid fragment encodes a polypeptide whose direct or indirect interaction with the Pi-ta resistance protein is responsible for triggering the Pi-ta resistance gene mediated defense response.

An "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms "subfragment that is functionally equivalent" "functionally equivalent subfragment", "functionally equivalent subsequence" and "subsequence" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the approropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the isolated nucleic acid fragment of the invention. Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151–153) with the default parameters (GAP PENALTY=10, GAP LENGTH PENALTY=10). Default parameters for pairwise alignments and calculation of percent identiy of protein sequences using the Clustal method are KTUPLE=1, GAP PENALTY=3, WINDOW=5 and DIAGONALS SAVED=5. For nucleic acids these parameters are GAP PENALTY=-10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402).

"Gene" refers to a nucleic acid fragment that expresses a functional RNA transcript, such as but not limited to mRNA, rRNA, tRNA, or antisense RNA, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising at least one regulatory sequence and coding sequence that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for an RNA transcript, and in the case of a gene encoding a polypeptide, a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Such sequences can be native or non-native. Regulatory sequences may include, but are not limited to, promoters, translation leader sequences, introns, and polyadenylation recognition sequences.

"Pathogen" refers to an organism or an infectious agent whose infection around or inside the cells of viable plant tissue elicits a disease response.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, 1989, *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., 1995, *Mol. Biotechnol.* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the klenow fragment of DNA polymerase I. "Sense" RNA refers to RNA transcript that includes the mRNA and so can be translated into protein within a cell or in vitro. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to at least one regulatory sequence in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (London) 327:70–73; U.S. Pat. No. 4,945,050), or an Agrobacterium-mediated method using an appropriate Ti plasmid containing the transgene (Ishida Y. et al., 1996, *Nature Biotech.* 14:745–750).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

An "expression construct" as used herein comprises any of the isolated nucleic acid fragments of the invention used either alone or in combination with each other as discussed herein and further may be used in conjunction with a vector or a subfragment thereof. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. The terms "expression construct" and "recombinant expression construct" are used interchangeably herein.

Cloned R-genes can be used to facilitate the construction of crop plants that are resistant to pathogens. In particular, transformation technology can be used to stack multiple single genes into an agronomic germplasm without linked genomic sequences that accompany genes transferred by classical breeding techniques. Cloned R-genes also can be used to overcome the inability to transfer disease resistance genes between plant species by classical breeding.

The present invention concerns an isolated nucleic acid fragment comprising a nucleic acid sequence or subsequence thereof encoding an altered Pi-ta resistance polypeptide wherein the polypeptide has a single amino acid alteration at position 918 which confers a resistance gene mediated defense response against a fungus comprising in its genome virulent and/or avirulent AVR-Pita alleles. In another aspect, the present invention provides an isolated nucleic acid fragment that has utility in controlling rice blast disease, caused by the fungus *Magnaporthe grisea*, in rice.

As discussed below, other subpopulations of *M. grisea* possess AVR-genes that are homologous to that contained in strains that elicit the Pi-ta specific defense response in rice. Demonstrations that AVR-genes which trigger a Pi-ta-resistance gene-mediated defense response can be present in *M. grisea* rice pathogens in subpopulation I, in Digitaria pathogens in subpopulation II, and in Pennisetum pathogens in subpopulation III, support broad utility for this gene in controlling *M. grisea* on the range of graminaceous hosts infected by this fungus.

Thus, it is believed that the isolated nucleic acid fragments of the invention will have utility in controlling diseases caused by a fungus comprising in its genome virulent and/or avirulent AVR-Pita alleles. For example, this invention will have utility in controlling diseases caused by *M. grisea* on other cereal crops including, but not limited to, wheat, barley, corn, finger millet, sorghum, and pearl millet.

Alternatively, some virulent avr-pita alleles encode substantially similar proteins (such as SEQ. ID NO:5 for G-198 and SEQ ID NO:13 for Ina 72.2) to the avirulent AVR-Pita protein and yet fail to trigger a Pi-ta-mediated resistance response. In its most extreme form, single amino acid substitutions introduced either through spontaneous mutations, or by in vitro mutagenesis, eliminate the ability of AVR-Pita to trigger a Pi-ta-resistance gene-mediated defense response.

The genetic cross (cross 4360) that identified the PWL2 gene, an AVR-gene controlling host species specificity on weeping lovegrass (Sweigard et al., 1995, *The Plant Cell* 7:1221), also segregated for an additional fungal gene that determined the ability of rice pathogens to infect rice variety Yashiro-mochi. This second AVR-gene, AVR-Pita (formerly called AVR2-YAMO for Yashiro-mochi) was inherited from the parental strain, 4224-7-8, and was derived from the Chinese field isolate O-137 (collected in 1985 at the China National Rice Research Institute in Hangzhou). In each of five complete tetrads derived from cross 4360, four of eight ascospore progeny were able to infect Yashiro-mochi and the others were not. Random spore analysis of cross 4360 and subsequent crosses confirmed segregation of AVR-Pita. Avirulent progeny from cross 4360 frequently produced a few fully pathogenic lesions on Yashiro-mochi. It was speculated that these rare lesions might be due to spontaneous mutations occurring at the AVR-Pita locus. Mutants that had lost function of AVR-Pita were isolated as described in Sweigard et al (1995, *The Plant Cell* 7:1221). These mutants that were now fully virulent toward Yashiro-mochi retained morphological and fertility characteristics as well as the MGR586 DNA fingerprinting profiles of the presumptive parent. The host specificities of the mutants toward rice varieties with other R-genes were unchanged.

Although dominance is not easy to assess for genes in predominantly haploid fungi like *M. grisea*, the occurrence of virulent mutants suggested that the expressed form of this AVR gene functions to stop infection of Yashiro-mochi, as predicted by the gene-for-gene hypothesis. The genetic instability of the AVR-Pita gene aided in its cloning. The AVR-gene was found to cosegregate with a cluster of physical markers including the telomeric repeat sequence at the end of a linkage group in the *M. grisea* RFLP map produced from cross 4360 (Sweigard et al., 1993, Genetic Maps, edited by S. J. O'Brien, Cold Spring Harbor Laboratory, pp 3.112–3.117). Spontaneous mutants that had become virulent on Yashiro-mochi rice showed structural changes in telomeric restriction fragments that mapped with the avirulence gene, suggesting the gene resided within 1 to 2 kb of the tip of the chromosome (Valent and Chumley, 1994, The Rice Blast Disease, edited by Zeigler, Leong and Teng, CAB International, Wallingford). Southern analysis of genomic DNA from wild type avirulent strains and from spontaneous mutants that had acquired deletions at the chromosome end, identified the sizes of the terminal chromosome fragment produced by digestion of genomic DNA with various restriction enzymes. This analysis suggested that the AVR-gene resided within a telomeric 6.5 kb BglII fragment that corresponded to the chromosome end. Cloning of the corresponding telomeric fragment allowed demonstration that it did indeed contain the AVR-Pita gene, which functioned to transform virulent pathogens of rice cultivar Yashiro-mochi into avirulent strains on Yashiro-mochi.

The AVR-Pita nucleic acid fragment isolated from the Chinese rice pathogen O-137 encodes a protein with 223 amino acids (SEQ ID NO:3). Amino acids 173–182 form a characteristic motif of a neutral zinc metalloproteinase and natural or in vitro mutation of the motif residues destroys AVR-gene activity, that is, it no longer transforms virulent strains of the pathogen to avirulence on rice variety Yashiro-mochi (Valent and Chumley, 1994, The Rice Blast Disease, edited by Zeigler, Leong and Teng, CAB International, Wallingford). The predicted amino acid sequence has low levels of homology to other metalloproteinases characterized from fungi (Genbank Accession numbers L37524 and S16547). The best characterized secreted fungal metalloprotease, NpII from *Aspergillus oryzae*, contains a 175 amino acid prepro-region that precedes a 177 amino acid mature region (Tatsumi et al., 1991, *Mol. Gen. Genet.* 228:97–103). The predicted AVR-Pita amino acid sequence exhibits 35% homology and 29% identity with NpII, with the most significant homology confined to the mature 177 amino acid form of NpII. In addition, alignment of the amino acid sequences of AVR-Pita and NpII showed conservation of the cysteines involved in disulphide bonds in the mature NpII protein. It was anticipated that the AVR-Pita isolated nucleic acid fragment encodes a preproprotein that is processed to a mature metalloprotease containing 176 amino acids. Based on this prediction, an AVR-Pita$_{176}$ expression construct was engineered to produce directly the putative mature protease for functional analyses.

Functional AVR-Pita nucleic acid fragments have been cloned from *M. grisea* strains that infect host plants other than rice, and are distantly related to rice pathogens in subpopulation Ia, including a Digitaria pathogen (JP34, also known as G-213, isolated in Japan) from subpopulation III, and a Pennisetum pathogen (BF17, isolated in Burkina Faso) from subpopulation IV. The AVR-Pita nucleic acid fragment cloned from the Digitaria pathogen (SEQ ID NO:14) corresponds to a translated amino acid sequence (SEQ ID NO:16) with 87.9% similarity and 84.7% identity to the O-137 AVR-Pita amino acid sequence when compared by the Bestfit algorithm of the University of Wisconsin Computer group package 9.1 (Devereux et al., 1984, *Proc Natl Acad Sci USA* 12:387–395). The G-213 AVR-Pita (avirulence) nucleic acid fragment has the most divergent sequence identified which retains the ability to transform virulent rice pathogens into avirulent strains that elicit a Pi-ta resistance gene mediated defense response. Conservation of AVR-gene function between distantly related *M. grisea* strains that infect different grass species suggests that a cloned Pi-ta resistance gene will be effective in controlling the blast fungus on its other host plants, in addition to rice. The present invention concerns an isolated nucleic acid fragment comprising a nucleic acid sequence or subsequence thereof encoding an altered Pi-ta resistance polypeptide wherein the polypeptide has a single amino acid alteration at position 918 which confers a resistance gene mediated defense response against a fungus comprising in its genome virulent and/or avirulent AVR-Pita alleles.

More specifically, it has been found that the single amino acid alteration at position 918 can be selected from the group consisting of methionine, cysteine, isoleucine, arginine, lysine, asparagine, leucine, and glutamine (M, C, I, R, K, N, L, and Q). As is shown in the examples below, this single amino acid alteration in susceptible and resistant forms of the Pi-ta resistance protein correlate with recognition specificity.

Alteration of the amino acid at position 918 makes it possible to generate mutant Pi-ta genes to recognize virulent AVR-Pita alleles for which no R-gene has currently been identified. Clearly, an ability to do so provides a valuable tool to control currently virulent strains of the rice blast fungus and other pathogens.

In another aspect this invention concerns chimeric genes comprising isolated nucleic acid fragments described herein operably linked to at least one regulatory sequence. Also of interest are plants transformed with such chimeric genes and seeds obtained from such plants.

Transgenic plants of the invention can be made using techniques well known to those of ordinary skill in the art, as is dicussed above, which are capable of mounting a resistance gene mediated defense response against a fungus comprising in its genome virulent and/or avirulent AVR-Pita alleles. Introduction of transgenes into plants, i.e., transformation is well known to those skilled in the art. A preferred method of plant cell transformation is the use of particle-accelerated or "gene gun" transformation technology (Klein et al. (1978) *Nature* (London) 327:70–73; U.S. Pat. No. 4,945,050). Examples of plants that can be transformed with such transgenes include, but are not limited to, monocots. Preferably, the monocot is a cereal. Most preferably, the monocot is rice, wheat, barley, corn, finger millet, sorghum, or pearl millet.

In still another aspect, this invention concerns a method of conferring a resistance gene mediated defense response in plants against a fungus comprising in its genome virulent and/or avirulent AVR-Pita alleles in plants which comprises: (a) transforming a plant with a chimeric gene of the invention; and (b) selecting transformed plants of step (a) which are resistant to a fungus comprising in it genome virulent and/or avirulent AVR-Pita alleles.

EXAMPLES

The present invention is further defined in the following Examples. From the above discussion and these Examples, one skilled in the art can ascertain the essential characteristics of this invention, and without departing from the spirit and scope thereof, can make various changes and modifications of the invention to adapt it to various usages and conditions.

Unless otherwise stated, all parts and percentages are by weight and degrees are Celsius. Techniques in molecular biology were typically performed as described in Sambrook, J., Fritsch, E. F. and Maniatis, T. 1989. Molecular cloning—A Laboratory Manual, $2^{nd}$ ed. Cold Spring Harbor Laboratory Press, Cold Spring Harbor, N.Y.

In some instances, amino acids are indicated by their one-letter designations widely used in the literature. For example A918 indicates that alanine (A) is at position 918 of the amino acid sequence of the protein.

Example 1

Pathogen Strain Development for Identification of the Corresponding R-Gene

An avirulent isolate of the pathogen is necessary to identify a host resistance gene, and the use of new pathogen strains may identify resistance genes that have so far escaped detection. Two fungal strains that show virulence (that is, they fail to elicit an R-gene mediated defense response) toward a rice variety with a particular R-gene are considered to lack the corresponding functional AVR-gene. However, although an avirulent strain of the fungus with a corresponding AVR-gene is necessary for identifying a host resistance gene, when two strains are avirulent toward a particular rice variety, they could have the same AVR-gene, or different AVR-genes triggering different R-gene mediated defense responses. Use of new or uncharacterized fungal strains may identify previously unidentified R-genes. This caution is especially required when working with field isolate rice pathogens such as O-137, the source of the AVR-Pita gene. In addition, rice blast infection assays are notoriously sensitive to environmental conditions, especially if the rice varieties have some level of general resistance to blast, or if the pathogens used are unstable in pathogenicity and morphology characteristics. Therefore, the use of thoroughly characterized pathogen strains is key to success.

Multiple pathogen resources, including genetic populations segregating for the AVR-Pita gene, facilitated cloning the Pi-ta gene. Progeny strains such as 4360-R-17, 4360-R-27, 4360-R-30, and subsequent generation strain 4375-R-26 (Sweigard et al., 1995, *The Plant Cell* 7:1221–1233) had improved characteristics for these studies. Because the rice crosses in these experiments had at least two R-genes segregating, Pi-ta and Pi-km, and because pathogen cross 4360 was segregating for AVR-genes corresponding to both known R-genes, there was a need to obtain genetically characterized pathogen strains bearing single AVR-genes. Such strains were needed to identify the effects of individual R-gene/AVR gene interactions on lesion development. There was also the need to maximize phenotypic differences between the resistant and susceptible interactions in order to assure accuracy of scoring the resistance phenotype among the rice progeny in the mapping population. Twenty-eight progeny strains were obtained from cross 4360 that contained AVR-Pita, but which did not contain AVR1-TSUY. It is believed that AVR1-TSUY is the AVR-gene corresponding to the blast resistance gene Pi-km in the japonica variety Tsuyuake (Yamada et al. (1976) *Ann. Phytopathol. Soc. Japan* 42: 216–219). These 28 progeny were screened for stable ability to produce fully susceptible disease symptoms (Type 4–Type 5 lesions) on one parental rice variety, and typical resistance responses (Type 0–Type 1 lesions) on the other rice variety (Valent et al., 1991, *Genetics* 127:87). *M. grisea* isolate 4360-R-62 was chosen as a test strain which contained only AVR-Pita. Out of an additional 9 strains screened, 4360-R-67 was chosen as an excellent pathogen that contains only AVR1-TSUY.

In addition, mutants that have lost AVR-gene function are useful for comparison to the parental strain from which they were derived. For example, strain CP987 (Sweigard et al. (1995) *The Plant Cell* 7:1221–1233) was derived from strain 4360-R-17 by isolation of a spontaneous virulent mutant. The AVR-Pita gene in CP987 was inactivated by a small deletion. Virulent mutants can easily be obtained from avirulent field isolates or laboratory strains as described in Sweigard et al. (1995) *The Plant Cell* 7:1221–1233. In the opposite direction of pathogen trait alteration, field isolate Guy11, which is virulent on Yashiro-mochi (Yamada et al. (1976) *Ann. Phytopathol. Soc. Japan* 42: 216–219), became avirulent on this host when it was transformed with a cloned AVR-Pita gene to produce strain CP3285. Fungal transformation in the rice blast system is routine, as described in Sweigard et al. (1995) *Plant Cell* 7:1221.

Example 2

Plant Infection and Evaluation

Infection assays were performed as previously described (Valent et al., 1991, *Genetics* 127:87). Conidia were collected from cultures grown on oatmeal agar plates by washing with a sterile 0.25% gelatin solution. Five to six individuals from each rice variety were sown in Metro-Mix® potting medium within plastic pots in a growth chamber. Plants were grown on a day cycle of 14 hours of light, 28 degrees and 70 to 85% relative humidity. Night conditions were 22 degrees and 85% relative humidity. Pots with two-week-old plants were placed into plastic bags in order to maintain 95–100% relative humidity required for pathogen penetration, and inoculated with pathogen strains such as but not limited to 4360-R-62 or 4360-R-67 described in Example 1. A four ml aqueous suspension, containing $2.5 \times 10^5$ conidia per ml, was sprayed onto the plants using an artist's air brush (Pasha, size 1). The plastic bags containing the inoculated plants were then closed with a twist-tie, and were incubated in low light conditions at room temperature for 24 hours. After 24 hours, the plants were removed from the bags, and were placed back in the growth chamber. Infection types, i.e., lesion symptoms, were scored 7 days after inoculation. A scale of 0–5 was used to classify infection phenotypes (Valent et al., 1991, *Genetics* 127:87–101). Lesion types of 0 and 1 were scored as resistant while lesion types 3 to 5 were scored as susceptible.

Example 3

Isolation of Nucleic Acid Fragments Encoding Avirulent and Virulent AVR-Pita Alleles Isolation of AVR-Pita Genomic Nucleic Acid Fragments The AVR-Pita genomic nucleic acid fragments from *M. grisea* strains O-137, Ina 72, GUY1, G-198 and G-213 are all believed to contain 3 introns within the AVR-Pita coding sequence. Southern blot analysis determined that strains O-137 and G-213 contain a single AVR-Pita gene whereas GUY11, G-198 and Ina 72 contain two AVR-Pita genes. To efficiently express the AVR-Pita nucleic fragment in rice leaves under the control of the CaMV 35S-Adh1 promoter, it was necessary to isolate the cDNA. AVR-Pita nucleic acid fragments have been cloned and/or sequenced from *M. grisea* strains O-137, G-213, GUY11, G-198 and two from Ina 72, and it is possible to use any of them to prepare AVR-Pita$_{176}$ nucleic acid fragments for the transient expression experiments.

Cloning of the AVR-Pita Gene from Strain O-137 by Cloning a Telomere Fragment

AVR-Pita was mapped to one end of *M. grisea* linkage group 2c of the O-137-derived progeny strain 4224-7-8 (Sweigard et al., 1993. In Genetic Maps, 6$^{th}$ edition, S. J. O'Brien, ed., Cold Spring Harbor Laboratory Press, pp.3.112–3.117). In this analysis, the AVR-Pita gene co-segregated with the telomere repeat sequences at the end of the chromosome. Identification of telomeric DNA fragments was routinely performed. Standard protocols were used for restriction enzyme digestions, RNA and DNA gel blot analysis (Sambrook; Ausubel et al., 1994, Current Protocols in Molecular Biology, Greene Publishing Associates/Wiley Interscience, New York) except as noted below for hybridizations with the oligonucleotide probe. The oligonucleotide [5'-(AACCCT)$_4$-3'] was synthesized and radiolabeled by kinase treatment with γ-$^{32}$P-ATP for detection of the hexameric telomere repeat sequence by DNA gel blot analysis. Genomic DNAs were prepared as described (Sweigard et al., 1995, *Plant Cell* 7:1221–1233), digested with restriction enzymes, electrophoresed on 0.7% agarose gels, and blotted to Hybond-N membranes. For hybridization with the telomeric repeat oligonucleotide, membranes were prehybridized in 6×SSPE, 5×Denhardts, 0.5% SDS, 100 g/ml ssCT DNA for 2 hrs at 42° C., and hybridized with radiolabeled oligonucleotide overnight at 42° C. Membranes were washed first for 10 minutes in 2×SSPE, 0.1%SDS at room temperature and then for 15 minutes in the same solution at 30–34° C.

Changes in the sizes of telomeric restriction fragments that correlated with a loss of avirulence toward Yashiromochi suggested the AVR-Pita gene is located directly adjacent to its linked telomere. Because cosmid libraries were unlikely to contain chromosome ends, we decided to clone this telomere specifically. Genomic DNA from the avirulent parental strain 4224-7-8 (Sweigard et al., 1995, *The Plant Cell* 7:1221–1233) was first treated with BAL31 nuclease in order to remove any 3' overhang of the G-rich strand and produce a blunt end at the telomere. The genomic DNA was treated with 0.125 units/ml of BAL31 nuclease (New England Biolabs, Inc.) for 50 min at 30° C. as described (Richards and Ausubel (1988) *Cell* 53:127–136). Under these conditions, no visible decrease occurred in the size of the telomeric fragments as determined by DNA gel blot analysis. An enriched fraction of genomic DNA that would contain the telomere fragment was produced based on our deduction that the 6.5 kb-BglII telomeric fragment that contains AVR-Pita does not contain any SalI sites. The Bal31 treated DNA was digested with the restriction enzymes BglII and SalI and subjected to electrophoresis on a 0.8% low melting agarose gel, and used to create a genomic sub-library of 6- to 7-kb fragments. DNA fragments in the size range of 7- to 8-kb were eluted from the gel and ligated into the BamHI and EcoRV polylinker sites of pBluescript SK(+). The sub-library was screened for telomere-containing clones using the telomeric oligonucleotide, and positive clones were analyzed further. A single clone, designated pCB780, was obtained with the predicted restriction fragments.

The AVR-Pita gene was identified in pCB780 by its ability to transform *M. grisea* virulent strains to avirulence towards rice containing Pi-ta. Fungal transformation for complementation analysis for function in conferring avirulence activity was performed as described (Sweigard et al., 1995, *Plant Cell* 7:1221–1233). To increase stability of the clone in *M. grisea*, pCB780 was cut with KpnI and partially digested with exonuclease III, resulting in plasmid pCB806 which had 123 bp of the telomeric repeat (almost the entire repeat) deleted. pCB806 was then cut with NcoI and XbaI to delete 4.5 kb of insert DNA, and the remaining insert (1928 bp) and vector was blunted and re-ligated to create pCB813 which was confirmed to contain an intact AVR-Pita gene using the functional assay described above. Nucleotide sequence of the insert in pCB813 (2 kb) was obtained, and used as basis of some of the oligonucleotide primers described herein (e.g., LF2C and LF2D).

Isolation of an AVR-Pita cDNA for the O-137 Allele AVR-Pita did not appear to be transcribed at detectable levels during axenic growth of the fungus in culture. We therefore subcloned the AVR-Pita genomic coding sequence into a constitutive expression vector, pCB963, under the control of the Aspergillus TrpC promoter and terminator (Staben et al., 1989). Strains transformed with pCB963 and grown in liquid culture expressed AVR-Pita as determined by RNA gel blot analysis using the DraIII—EcoRI fragment from pCB780 as a probe. A cDNA clone obtained from this transformed strain confirmed the positions of the three predicted introns.

Specifically, the constitutive expression vector, pCB963, was produced as follows. The vector pCSN43 (Staben et al. (1989) *Fungal Genet Newslett* 36:79–81) was first modified to eliminate extra BamHI and ClaI sites by deletion of the smaller MluI-SacI fragment. The AVR-Pita genomic coding sequence was cloned by PCR using oligonucleotides LF2C (SEQ ID NO:17) and LF2D (SEQ ID NO:18), designed to place a ClaI site (underlined in SEQ ID NO:17 below) at the start ATG and a BamHI site (underlined in SEQ ID NO:18 below) at the telomere end.

LF2C: 5'-GATCGA<u>ATCGAT</u>ATGCTT TTTTATTCATTA TTTTTTTTTC-3' (SEQ ID NO:17)

LF2D: 5'-GATCGA<u>GGATCC</u>CCCTCTATTGTT AGATTG ACC-3' (SEQ ID NO:18)

The coding sequence of HPH in pCSN43 was then removed by digestion with ClaI and BamHI and the ClaI/BamHI fragment containing the AVR-Pita genomic coding sequence was inserted to produce pCB963.

Transgenic fungus containing pCB963 was grown in liquid culture for purification of RNA. The Perkin Elmer Cetus—GeneAmp RNA PCR kit protocol was used to reverse transcribe RNA using random hexamer priming followed by PCR amplification of cDNA using oligonucleotides LF2C (SEQ ID NO:17) and LF2D (SEQ ID NO:18). The cDNA fragment encoding AVR-Pita was digested with ClaI and BamHI and cloned into ClaI/BamHI-cut pBluescript SK+ (Stratagene) to produce pCB979.

A 486 bp functional promoter fragment was amplified from the O-137 genomic DNA clone pCB813 using primers LF2H (SEQ ID NO:19) and LF12 (SEQ ID NO:20).

LF2H: 5'-AAGCATATCGATAAAAATAATGTTAATT GTGCAG-3' (SEQ ID NO:19)

LF12: 5'-GCCGAGTCGTTCTGAGGG-3' (SEQ ID NO:20)

The 672 bp PCR product was end-filled using Klenow polymerase (Sambrook), digested with ClaI and cloned into the ClaI and HincII sites of pCB979 to create pCB980.

Cloning of AVR-Pita Genomic Coding Sequences from Other Fungal Strains

Genomic coding sequences were amplified from genomic DNA isolated from strains G-198, Ina 72 and G-213 using primers LF2C (SEQ ID NO: 17), LF2D (SEQ ID NO:18), LF2C* (SEQ ID NO:21), GB84 (SEQ ID NO:22) and GB85 (SEQ ID NO:23) as shown in Table 3.

LF2C*: 5'-GATCGAATCGATATGCTTTTTTATTCATTGT TATTTTATTTC-3' (SEQ ID NO:21)

GB84: 5'-CCCTGGGATCCAACACTAACGTTAT TTAACA-3' (SEQ ID NO:22)

GB85: 5'-GCCGCATCGATATGCTTTTTTATTCATTTAT ATTTTA-3'(SEQ ID NO:23)

In each case, the 960 bp PCR product obtained was digested with BamHI and ClaI. pCB980 was also digested with BamHI and ClaI, and the 3394 bp fragment containing both the functional AVR-Pita promoter from strain O-137 and pBluescript SK+ vector sequences was gel-purified. The digested 945 bp PCR product was then cloned into the 3394 bp vector fragment. This cloning step essentially replaced the 725 bp O-137 AVR-Pita cDNA fragment with each of the genomic AVR-Pita nucleic acid fragments from G-198, Ina72 and G-213.

TABLE 3

Construction of Plasmids Containing AVR-Pita Genomic Fragments From Various *M. grisea* Strains

| AVR-Pita Allele | Phenotype | Primers used for PCR | Resulting Plasmid |
|---|---|---|---|
| G-198 | Virulence | LF2C (SEQ ID NO:17), LF2D (SEQ ID NO:18) | pCB1447 |
| Ina72.1 | Avirulence | LF2D (SEQ ID NO:18), LF2C* (SEQ ID NO:21) | pCB2076 |
| Ina72.2 | Virulence | LF2D (SEQ ID NO:18), LF2C* (SEQ ID NO:21) | pCB2077 |
| G-213 | Avirulence | GB84 (SEQ ID NO:22), GB85 (SEQ ID NO:23) | pCB1965 |

All genomic AVR-Pita nucleic acid fragments isolated thus far are believed to contain the three intron sequences. Predicted splicing of the introns was again confirmed by isolation of a cDNA clone encoding AVR-Pita of G-198 as described below. The cDNA sequence for the G-198 allele is set forth in SEQ ID NO:4. For all other AVR-Pita clones, the three intron sequences may be removed to generate a cDNA clone, using the appropriate oligonucleotides, subcloning and/or PCR techniques well known to those skilled in the art. The AVR-Pita genomic sequences from Ina 72 are set forth in SEQ ID NO:8 (Ina 72.1) and SEQ ID NO:11 (Ina 72.2), and corresponding predicted cDNA sequences derived from these genomic sequences are respectively set forth in SEQ ID NO:9 and SEQ ID NO:12. The genomic sequence of the AVR-Pita nucleic acid fragment from G-213 is set forth in SEQ ID NO:14, and a predicted cDNA sequence of AVR-Pita from G-213 derived from SEQ ID NO:14 is set forth in SEQ ID NO:15.

To obtain the sequence of a virulent allele from GUY11, an AVR-Pita nucleic acid fragment was amplified from genomic GUY11 DNA by PCR using primers LF2D (SEQ ID NO:18) and LF2C (SEQ ID NO:17). The PCR product was sequenced directly after purification using a QIAquick™ PCR Purification Kit (Qiagen) The genomic sequence thus obtained is set forth in SEQ ID NO:59.

FIG. 1 is an alignment of the AVR-Pita amino acid sequences derived from nucleotide sequences obtained from *M. grisea* strains O-137, G-213, Ina 72, G-198, and GUY11. Isolation of AVR-Pita cDNA Nucleic Acid Fragments for Expression of the Putative Mature Protease in Plants Infection assays using pathogen strains O-137 and G-198 were performed as previously described (Valent et al., 1991, *Genetics* 127:87) and as recited in Example 2.

pCB980 (SEQ ID NO:1) contains O-137 AVR-Pita cDNA, which was clone d using the method desribed above.

Plasmid pAVR3 contains nucleotides 139–672 of the AVR-Pita nucleic acid fragment (SEQ ID NO:2) from *M. grisea* strain O-137 encoding the predicted mature protease plus one additional N-terminal amino acid (AVR-Pita$_{177}$, beginning with Ile-47 of the preproprotein) and a start codon met fused to the 35S/Adh1-6 promoter in vector pML 142. The AVR-Pita nucleic acid fragment was amplified by PCR from AVR-Pita cDNA using primers AV1 (SEQ ID NO:24) an d AV3 (SEQ ID NO:25), digested with PmlI and KpnI, blunted with Klenow polymerase and cloned into pML142 that had also been cut with PmlI and KpnI and blunted with Klenow polymerase, resulting in pAVR3.

AV1: 5'-GCCGGCACGTGCCATGATTGAACGCTATTC CCAATG-3' (SEQ ID NO:24)

AV3: 5'-GCCGGGATCCCCCTCTATTGTTAGATTGAC-3' (SEQ ID NO:25)

The coding sequence for the predicted mature protease (beg inning with Glu-48 of the preproprotein) was obtained by PCR-amplification from the AVR-Pita nucleic acid fragment (SEQ ID NO:2) in plasmid pAVR3 using oligonucleotides YL30 containing an in-frame NcoI site (SEQ ID NO:26) and YL37 (SEQ ID NO:27).

YL30: 5'-ACAACAAGCCGGCACGTGCCATGG AACGCT-3' (SEQ ID NO:26)

YL37: 5'-TCCTTCTTTAGGTACCGCTCTCTC-3' (SEQ ID NO:27)

The PCR fragment was cloned NcoI/KpnI into pML142 resulting in vector pCB1947. This was done to eliminate the Ile-47 codon (aft) in pAVR3 and generate AVR-Pita$_{176}$. Additional details are described in PCT Publication No. WO 00/08162, the disclosure of which is hereby incorporated by reference.

To isolate AVR-Pita cDNA nucleic acid fragments from strain G-198, plasmid pCB1447 was transformed into *M. grisea* strain CP987 and transformants containing this plasmid were used to infect susceptible Tsuyuake rice. Nucleic acid fragments comprising the AVR-Pita cDNA coding sequence from strain G-198 was amplified by RT-PCR from mRNA isolated from infected rice leaf tissue 72 hours after inoculation with 2×10$^6$ spores ml$^{-1}$ of *M. grisea* strain CP3402 (CP987 transformed with pCB1447) using primers GB183 (SEQ ID NO:28) and GB184 (SEQ ID NO:29) containing NcoI and Kpn sites, respectively.

GB183: 5'-GGGCTTCCATGGAACGCTATTCCCAAT GTTCAG-3' (SEQ ID NO:28)

GB184: 5'-CACTAAGGTACCTTAACATATTTATAAC GTGCAC-3' (SEQ ID NO:29)

The PCR product was digested with NcoI and KpnI and this was cloned into pML142 (described in WO 00/08162). pML 142 had also been digested with NcoI and KpnI and the 5.1 kb fragment isolated and purified from an agarose gel. The digested G-198 PCR nucleic acid fragment was ligated with the 5.1 kb pML 142 nucleic acid fragment using techniques familiar to those skilled in the art to generate plasmid pCB2148.

Example 4

Mutagenesis of Pi-ta at Position 918 to Create a Library of Pi-ta Plasmids With all 20 Amino Acids Represented at Position 918

Mutating the Pi-ta gene at codon 918 to create a set of modified Pi-ta genes with each of the 20 amino acids represented at position 918 required a two step process which is described below. Two amino acids were already represented, A918 (alanine at position 918) occurs in resistant forms of Pi-ta while S918 (serine at position 918) occurs in susceptible forms.

A full-length Pi-ta cDNA fragment was cloned using reverse transcriptase (RT) PCR and subcloning. The approach involved isolating mRNA from transgenic Nipponbare line 27-4-8-1 which contained a transgene comprising a genomic Pi-ta nucleic acid fragment from *Oryza sativa* variety Yashiro-mochi operably linked to the CaMV 35S promoter (described in WO 00/01862, Example 10, expression construct 3) and which was shown on a northern blot to overexpress Pi-ta. First strand cDNA was synthesized using the isolated mRNA fraction as template and the oligonucleotide GB67 (SEQ ID NO:30) as primer.

GB67:5'-CCATTAAGCTTGGTTTCAAACAATC-3' (SEQ ID NO:30).

A partial Pi-ta cDNA (2.1 kb) was amplified from first strand cDNA using primers F12-1 (SEQ ID NO:31) and GB67 (SEQ ID NO:30).

F12-1: 5'-GTGGCTTCCATTGTTGGATC-3' (SEQ ID NO:31)

It was then cloned into pSL1180 (Pharmacia) using the BamHI (restriction site present in the Pi-ta nucleic acid fragment) and HindIII (restriction site present in GB67 sequence) cloning sites. To obtain a full-length synthetic cDNA, a 706 bp NcoI-BamHI fragment containing the 5' end of the Pi-ta coding sequence was isolated from pCB1649 (described in WO 00/08162) and cloned into the NcoI-BamHI site upstream of the 2090 bp BamHI-HindIII partial Pi-ta cDNA fragment to create a full-length promoter-less Pi-ta cDNA. DNA sequence analysis determined that there was a 2 bp deletion present at codon 796 (probably a PCR artifact) resulting in a frameshift mutation that would have truncated the predicted Pi-ta protein by 119 amino acids. This was corrected by replacing a 1400 bp SphI-BglII fragment with the corresponding fragment from pCB1649 which contained the correct sequence, to create pCB1906. DNA sequence analysis also determined that the predicted intron was precisely spliced in this synthetic cDNA. A native Pi-ta promoter fragment (2425 bp) was added by cloning a 3173 bp EcoRI fragment from pCB1649 into the EcoRI sites of pCB1906, resulting in plasmid pCB1926 which contained the final Pi-ta cDNA construct (FIG. 2C) comprising 2425 bp of the native Pi-ta promoter (nucleotides 1 to 2425 in SEQ ID NO:57) and Pi-ta cDNA (nucleotides 2426–5212 in SEQ ID NO:57) from rice variety Yashiro-mochi. The deduced amino acid sequence of the protein encoded by this particular Pi-ta cDNA is set forth in SEQ ID NO:58.

Plasmid pCB2020 was produced by amplifying a susceptible Pi-ta nucleic acid fragment from susceptible C101A51 rice (Mackill and Bonman (1992) *Phytopathology* 82:746–749) genomic DNA in a PCR reaction using primers GB61 (SEQ ID NO:32) and GB67 (SEQ ID NO:30).

GB61: 5'-CAATGCCGAGTGTGCAAAGA-3' (SEQ ID NO:32)

The resulting 440 bp PCR fragment was digested with BglII and HindIII and cloned into plasmid pCB1926 that had been digested with the same enzymes (and the corresponding 4900 bp nucleic acid fragment isolated and purified from an agarose gel). This cloning step produced plasmid pCB2020 which is identical to pCB1926 except that codon 918 encodes S and not A.

The remaining 18 amino acid modifications were introduced into Pi-ta by first amplifying the fragment from plasmid pCB1926 using PCR primer GB60 (SEQ ID NO:33) and a set of 18 primers GB164–GB179, GB181 and GB182 (SEQ ID NOS:34–51) in 18 separate PCR reactions, one for each primer.

GB60: 5'-CAATGCCGAGTGTGCAAAGG-3 (SEQ ID NO:33)

GB164: 5'-AGGCGAGTCGACGTTTCAAACAATCATC AAGTCAGGTTGAAGA TGCATCTCAGGTAAAGAT AGAAGC-3' (SEQ ID NO:34)

GB165: 5'-AGGCGAGTCGACGTTTCAAACAATCA TCAAGTCAGGTTGAAGATGCATATCAGGTAA AGATAGAAGC-3' (SEQ ID NO:35)

GB166: 5'-AGGCGAGTCGACGTTTCAAACAATCA TCAAGTCAGGTTGAAGATGCATCCTAGGTAAA GATAGAAGC-3' (SEQ ID NO:36)

GB167: 5'-AGGCGAGTCGACGTTTCAAACAATC ATCAAGTCAGGTTGAAGATGCATCTTAGGTAAA GATAGAAGC-3' (SEQ ID NO:37)

GB168: 5'-AGGCGAGTCGACGTTTCAAACAATC ATCAAGTCAGGTTGAAGATGCATATTAGGTAAA GATAGAAGC-3' (SEQ ID NO:38)

GB169: 5'-AGGCGAGTCGACGTTTCAAACAATCA TCAAGTCAGGTTGAAGATGCATCATAGGTAAA GATAGAAGC-3' (SEQ ID NO:39)

GB170: 5'-AGGCGAGTCGACGTTTCAAACAATCA TCAAGTCAGGTTGAAGATGCATAATAGGTAAA GATAGAAGC-3' (SEQ ID NO:40)

GB171: 5'-AGGCGAGTCGACGTTTCAAACAATC ATCAAGTCAGGTTGAAGATGCATTGTAGGTAAA GATAGAAGC-3' (SEQ ID NO:41)

GB172: 5'-AGGCGAGTCGACGTTTCAAACAATCA TCAAGTCAGGTTGAAGATGCATCCAAGGTAAA GATAGAAGC-3' (SEQ ID NO:42)

GB173: 5'-AGGCGAGTCGACGTTTCAAACAATCA TCAAGTCAGGTTGAAGATGCATACAAGGTAAA GATAGAAGC-3' (SEQ ID NO:43)

GB174: 5'-AGGCGAGTCGACGTTTCAAACAATC ATCAAGTCAGGTTGAAGATGCATGTAAGGTAAA GATAGAAGC-3' (SEQ ID NO:44)

GB175: 5'-AGGCGAGTCGACGTTTCAAACAATCA TCAAGTCAGGTTGAAGATGCATGAAAGGTAAA GATAGAAGC-3' (SEQ ID NO:45)

GB176: 5'-AGGCGAGTCGACGTTTCAAACAATC ATCAAGTCAGGTTGAAGATGCATTTGAGGTAAA GATAGAAGC-3' (SEQ ID NO:46)

GB177: 5'-AGGCGAGTCGACGTTTCAAACAATC ATCAAGTCAGGTTGAAGATGCATGTGAGGTAAA GATAGAAGC-3' (SEQ ID NO:47)

GB178: 5'-AGGCGAGTCGACGTTTCAAACAATCA TCAAGTCAGGTTGAAGATGCATCAGAGGTAAA GATAGAAGC-3' (SEQ ID NO:48)

GB179: 5'-AGGCGAGTCGACGTTTCAAACAATCA TCAAGTCAGGTTGAAGATGCATCGGAGGTAAA GATAGAAGC-3' (SEQ ID NO:49)

GB181: 5'-AGGCGAGTCGACGTTTCAAACAATCATCAAG TCAGGTTGAAGATCATGCCAGGTAAAGA TAGAAGC-3' (SEQ ID NO:50)

GB182: 5'-AGGCGAGTCGACGTTTCAAACAATCATCAAG TCAGGTTGAAGATGCATAACAGGTAAA GATAGAAGC-3' (SEQ ID NO:51)

The resulting 440 bp PCR nucleic acid fragments were digested with BglII and SalI and the 322 bp fragment ligated into plasmid pCB2114 (described below) that had been digested with the same enzymes. This replaced the resistant Pi-ta 322 bp BglII-SalI fragment in plasmid pCB2114 with a nucleic acid fragment containing the altered codon at position 918. This cloning step produced plasmids pCB2153–pCB2170 (Table 4). Plasmid pCB2114 comprises nucleotide sequence encoding the Pi-ta leucine rich domain (LRD) described in WO 00/01862 which was amplified in a PCR reaction with primers GB47 (SEQ ID NO:52) and GB107 (SEQ ID NO:53). The 1050 bp PCR fragment was digested with EcoRI and SalI and cloned into plasmid pGAL4-BD-Cam (Stratagene) that had been digested with the same enzymes.

GB47: 5'-AATGCAGAATTCACAACACCACTAGCAG GTTTG3' (SEQ ID NO:52)

GB107: 5-AGGCGAGTCGACGTTTCAAACAATCAT CAAGTCAGG-3' (SEQ ID NO:53)

The second cloning step required the modified Pi-ta fragment in plasmids pCB2153–pCB2170 to be amplified with primers GB60 (SEQ ID NO:33) and GB67 (SEQ ID NO:30) in 18 separate PCR reactions. GB67 (SEQ ID NO:30) adds a HindIII cloning site after the TGA stop codon. The resulting 18 PCR fragments were digested with BglII and HindIII and cloned into plasmid pCB1926 that had been digested with the same enzymes (and the corresponding 4900 bp nucleic acid fragment isolated and purified from an agarose gel). This cloning step generated plasmids pCB2171–pCB2188 (Table 4). Table 4 identifies the plasmids with respect to the amino acid at position 918 of the Pi-ta protein encoded by the nucleic acid fragments contained in the plasmids. For example, the table indicates that pCB2153 (line 3) contains a nucleic acid fragment encoding a Pi-ta protein in which the amino acid at position 918 is a glutamic acid residue (E) instead of an alanine residue (A); this change was brought about by changing the Pi-ta nucleotide sequence via PCR as described above using oligonucleotides SEQ ID NO:33 and SEQ ID NO:34 (column 2). Plasmid pCB2153 was then used to make pCB2171 (column 4) as described above; pCB2171 was the one actually used ("transient assay plasmid") in the transient assay experiments described in Example 5. The sequence of each of these plasmids was verified by sequencing using primers that are enclosed in Example 7 in WO 00/01862. This resulting set of plasmids pCB2171–pCB2188, pCB1926 and pCB2020 represented a Pi-ta nucleic acid fragment with all 20 possible amino acid combinations at position 918 linked to a native 2424 bp Pi-ta promoter nucleic acid fragment.

TABLE 4

Construction of Nucleic Acid Fragments Encoding Pi-ta Proteins With All Possible 20 Amino Acids Represented at Position 918 of the Pi-ta Protein

| Plasmid | Oligonucleotide used with SEQ ID NO:33 in PCR to introduce amino acid alteration | Amino Acid Alteration | Use |
| --- | --- | --- | --- |
| pCB1926 | — | Pi-ta (resistant)$A_{918}$ | Transient assay plasmid |
| pCB2020 | — | Pi-ta (susceptible) $S_{918}$ | Transient assay plasmid |
| pCB2153 | SEQ ID NO:34 | $A_{918}$-E | Progenitor to pCB2171 |
| pCB2154 | SEQ ID NO:35 | $A_{918}$-D | Progenitor to pCB2172 |
| pCB2155 | SEQ ID NO:36 | $A_{918}$-R | Progenitor to pCB2173 |
| pCB2156 | SEQ ID NO:37 | $A_{918}$-K | Progenitor to pCB2174 |
| pCB2157 | SEQ ID NO:38 | $A_{918}$-N | Progenitor to pCB2175 |
| pCB2158 | SEQ ID NO:39 | $A_{918}$-M | Progenitor to pCB2176 |
| pCB2159 | SEQ ID NO:40 | $A_{918}$-I | Progenitor to pCB2177 |
| pCB2160 | SEQ ID NO:41 | $A_{918}$-T | Progenitor to pCB2178 |
| pCB2161 | SEQ ID NO:42 | $A_{918}$-W | Progenitor to pCB2179 |
| pCB2162 | SEQ ID NO:43 | $A_{918}$-C | Progenitor to pCB2180 |
| pCB2163 | SEQ ID NO:44 | $A_{918}$-Y | Progenitor to pCB2181 |
| pCB2164 | SEQ ID NO:45 | $A_{918}$-F | Progenitor to pCB2182 |
| pCB2165 | SEQ ID NO:46 | $A_{918}$-Q | Progenitor to pCB2183 |
| pCB2166 | SEQ ID NO:47 | $A_{918}$-H | Progenitor to pCB2184 |
| pCB2167 | SEQ ID NO:48 | $A_{918}$-L | Progenitor to pCB2185 |
| pCB2168 | SEQ ID NO:49 | $A_{918}$-P | Progenitor to pCB2186 |
| pCB2169 | SEQ ID NO:51 | $A_{918}$-V | Progenitor to pCB2187 |
| pCB2170 | SEQ ID NO:50 | $A_{918}$-G | Progenitor to pCB2188 |
| pCB2171 | SEQ ID NO:34 | $A_{918}$-E | Transient assay plasmid |
| pCB2172 | SEQ ID NO:35 | $A_{918}$-D | Transient assay plasmid |
| pCB2173 | SEQ ID NO:36 | $A_{918}$-R | Transient assay plasmid |

TABLE 4-continued

Construction of Nucleic Acid Fragments Encoding Pi-ta Proteins With All Possible 20 Amino Acids Represented at Position 918 of the Pi-ta Protein

| Plasmid | Oligonucleotide used with SEQ ID NO:33 in PCR to introduce amino acid alteration | Amino Acid Alteration | Use |
| --- | --- | --- | --- |
| pCB2174 | SEQ ID NO:37 | $A_{918}$-K | Transient assay plasmid |
| pCB2175 | SEQ ID NO:38 | $A_{918}$-N | Transient assay plasmid |
| pCB2176 | SEQ ID NO:39 | $A_{918}$-M | Transient assay plasmid |
| pCB2177 | SEQ ID NO:40 | $A_{918}$-I | Transient assay plasmid |
| pCB2178 | SEQ ID NO:41 | $A_{918}$-T | Transient assay plasmid |
| pCB2179 | SEQ ID NO:42 | $A_{918}$-W | Transient assay plasmid |
| pCB2180 | SEQ ID NO:43 | $A_{918}$-C | Transient assay plasmid |
| pCB2181 | SEQ ID NO:44 | $A_{918}$-Y | Transient assay plasmid |
| pCB2182 | SEQ ID NO:45 | $A_{918}$-F | Transient assay plasmid |
| pCB2183 | SEQ ID NO:46 | $A_{918}$-Q | Transient assay plasmid |
| pCB2184 | SEQ ID NO:47 | $A_{918}$-H | Transient assay plasmid |
| pCB2185 | SEQ ID NO:48 | $A_{918}$-L | Transient assay plasmid |
| pCB2186 | SEQ ID NO:49 | $A_{918}$-P | Transient assay plasmid |
| pCB2187 | SEQ ID NO:51 | $A_{918}$-V | Transient assay plasmid |
| pCB2188 | SEQ ID NO:50 | $A_{918}$-G | Transient assay plasmid |

Example 5

Transient Particle Bombardment Assay for Testing Efficacy of Triggering Pi-ta Mediated Resistance by Modified Pi-ta Genes Toward the Virulent AVR-Pita Allele from M. grisea Strain G-198

Particle Bombardment Demonstrates that AVR-Pita from avirulent M. grisea Strain O-137 But Not avr-pita from virulent M. grisea Strain G-198 Elicits a Hypersensitive Response in Resistant Rice containing Pi-ta As is standard practice to those skilled in the art, high velocity biolistic bombardment of plant tissue with particles coated with recombinant expression constructs of interest results in transient expression of the nucleic acid fragments from the introduced plasmids. Function of disease resistance genes can be demonstrated in transient leaf bombardment experiments using reporter gene expression to assay for triggering of the hypersensitive cell death resistance response. Such an assay has demonstrated utility for analyzing function of the Pi-ta resistance gene and is described in WO 00/08162.

In order to overcome the obstacle to uniform incorporation of the fungal AVR-gene within the plant tissue, introduction of an AVR-Pita expression construct was tested by co-bombardment along with the GUS reporter gene. In particular, constructs were engineered that express the putative mature protease (AVR-Pita$_{176}$) from strains O-137 (pCB1947) and G-198 (pCB2148) under control of the 35S promoter for constitutive expression in plant cells.

To determine if co-expression of the AVR-Pita$_{176}$ construct from strains O-137 and G-198 triggers Pi-ta mediated defense responses when introduced into Pi-ta-containing plant cells, seedlings from Pi-ta-plants (Yashiro-mochi and YT14) and plants that lack Pi-ta (Nipponbare and YT16) were co-bombarded with pCB1947 or pCB2148 containing the 35S/Adh1-6::AVR-Pita$_{176}$ gene construct and pML63 (which is described in WO 00/08162) containing the 35S::GUS reporter gene. YT14 and YT16 are described in WO 00/08162. Nipponbare is a rice variety that is widely studied (e.g., Mao et al. (2000) Genome Res 10:982–990). Seeds were germinated on leaf assay media: ½ strength MS medium (Murashige and Skoog, 1962, Physiol. Plant.

15:473–497) supplemented with 100 mg casein hydrolysate and 0.5% agarose for a week in an incubator at 25° C. for 48 hours in 12 hr photoperiod with a 100 $\mu Em^{-2}s^{-1}$ of cool, white light. Two-leaf seedlings were excised from the agar medium using a surgical razor and placed in a petri dish containing a prewetted filter paper. Plantlets were labeled at the base with a permanent marker for identification. Biolistic bombardment of the seedlings was performed using Bio-Rad PDS-1000/He apparatus and 1150-psi rupture disks. Gold particles (0.6 $\mu$m diameter) were prepared according to the instructions provided by the manufacturer. For each cobombardment, 1 $\mu$g of gold particles was coated with 1.5 $\mu$g of 35S/GUS and 1 $\mu$g of other plasmids. After bombardment, seedlings were maintained at 25° C. for 48 hours in Petri dishes containing prewetted filter paper. Leaves were cleared in 70% ethanol and histochemically assayed for β-Glucuronidase (GUS) activity using 5-bromo-4-chloro-3-indolyl glucuronide (X-gluc) as a substrate (Jefferson, 1987, Plant Mol. Bio. Rep. 5:387–405).

The AVR-Pita$_{176}$ expression construct pCB1947 mediated a striking decrease in GUS expression (suggesting cell death prior to expression), when cobombarded with the GUS construct into YT14 leaves containing the endogenous Pi-ta gene. This effect was not observed in susceptible YT16 leaves treated the same way. A virulent form of AVR-Pita$_{176}$ in construct pCB2148 failed to decrease GUS expression in either resistant TY14 or susceptible YT16 leaves. Thus, only expression of the AVR-Pita coding sequence from O-137 triggers the rice defense response when introduced directly into rice leaves containing the endogenous Pi-ta gene.

In the second part of this experiment, a third construct was added, pCB1926. Seedlings from Pi-ta-plants (Yashiromochi and YT14) and plants that lack Pi-ta (Nipponbare and YT16) were co-bombarded with the 35S/Adh1-6::AVR-Pita$_{176}$ gene construct pCB1947 or pCB2148, the Pi-ta cDNA under the control of its native promoter (pCB1926) and the 35S::GUS reporter gene. In this case susceptible YT16 rice leaves responded in the same way as resistant YT14 rice leaves to the avirulent AVR-Pita$_{176}$ construct from strain O-137. It is therefore possible to add Pi-ta exogenously to susceptible rice leaves to elicit a HR response to AVR-Pita. No HR response was observed towards the virulent avr-Pita construct from virulent strain G-198.

This assay forms the basis for the next experiment described where 18 new Pi-ta variants described in Example 4 above were then tested for their ability to encode a novel Pi-ta protein that responds to virulent avr-Pita proteins to elicit an HR.

Testing Pi-ta Transient Expression Vectors Encoding Pi-ta Proteins Altered at Position 918

The 20 vectors pCB1926, pCB2020 and pCB2171–pCB2188 described in Example 4 above were tested in the transient assay using the conditions described above. All were co-bombarded with pML63 which contains a 35S::GUS reporter gene and either pCB1947 or pCB2148 which contain different 35S/Adh1-6::AVR-Pita$_{176}$ gene constructs. Results are summarized in Table 5. In the table, "−" indicates lack of GUS staining that is indicative of the hypersensitive response (there is productive recognition between the AVR-Pita and Pi-ta gene products); "+/−" indicates a few rare GUS loci that may indicate productive recognition between the AVR-Pita and Pi-ta gene products; "+" indicates a small number of GUS loci indicative of possible albeit suboptimal recognition between the AVR-Pita and Pi-ta gene products; and "++" and "+++" indicate multiple GUS loci indicative of no productive recognition between the AVR-Pita and Pi-ta gene products. Plates 1 and 2 represent two replicates for each AVR-Pita/Pi-ta combination, with each plate having two test seedlings. "Repeats" indicates the number of times a particular experiment was repeated.

TABLE 5

Effect of Amino Acid at Position 918 on Ability of Pi-ta to Recognize AVR-Pita from *M. grisea* strain O-137 and avr-pita from *M. grisea* strain G-198

GUS Activity @ 48 hr

| Pi-ta Constructs | AVR-Pita (O-137) (pCB1947) Plate 1 | Plate 2 | avr-pita (G-198) (pCB2148) Plate 1 | Plate 2 | No AVR gene Plate 1 | Plate 2 | Repeats | Conclusion |
|---|---|---|---|---|---|---|---|---|
| A$_{918}$ (Resistant) | − | − | + | ++ | | | 4 | resistant control - recognizes avirulent |
| S$_{918}$ (Susceptible) | ++ | ++ | + | ++ | | | 4 | susceptible control - no recognition |
| G$_{918}$ | ++ | +++ | ++ | ++ | | | 1 | not functional - no recognition |
| V$_{918}$ | ++ | ++ | + | ++ | | | 1 | not functional - no recognition |
| E$_{918}$ | − | + | − | ++ | | | 1 | not functional - no recognition |
| D$_{918}$ | +++ | +++ | + | + | | | 1 | not functional - no recognition |
| R$_{918}$ | − | − | − | + | | | 1 | recognizes avirulent-reduced recognition? |
| K$_{918}$ | − | + | − | − | | | 1 | recognizes virulent-reduced recognition? |
| N$_{918}$ | − | + | − | − | | | 1 | recognizes virulent-reduced recognition? |
| M$_{918}$ | − | − | − | − | ++ | ++ | 3 | recognizes both avirulent and virulent |
| I$_{918}$ | ++ | ++ | − | − | | | 3 | recognizes virulent - switched specificity |

TABLE 5-continued

Effect of Amino Acid at Position 918 on Ability of Pi-ta to Recognize
AVR-Pita from *M. grisea* strain O-137 and avr-pita from *M. grisea* strain G-198
GUS Activity @ 48 hr

| Pi-ta Constructs | AVR-Pita (O-137) (pCB1947) Plate 1 | Plate 2 | avr-pita (G-198) (pCB2148) Plate 1 | Plate 2 | No AVR gene Plate 1 | Plate 2 | Repeats | Conclusion |
|---|---|---|---|---|---|---|---|---|
| $H_{918}$ | + | + | + | + | | | 1 | not functional - no recognition |
| $L_{918}$ | +/− | +/− | +/− | +/− | | | 1 | recognizes both avirulent and virulent |
| $P_{918}$ | + | + | + | ++ | | | 1 | not functional - no recognition |
| $T_{918}$ | + | +/− | + | +/− | | | 1 | not functional - no recognition |
| $W_{918}$ | − | +/− | − | + | | | 1 | |
| $C_{918}$ | +/− | − | − | − | | | 2 | recognizes both avirulent and virulent |
| $Y_{918}$ | ++ | + | + | + | | | 1 | not functional - no recognition |
| $F_{918}$ | + | + | − | + | | | 1 | |
| $Q_{918}$ | + | + | − | − | | | 1 | recognizes avirulent-reduced recognition? |

Consistent with disease phenotypes observed when Yashiro-mochi is challenged with various *M. grisea* strains, Table 5 indicates that the Pi-ta protein from Yashiro-mochi (A918) recognizes the AVR-Pita protein from O-137 (which in planta results in disease resistance phenotype when Yashiro-mochi is challenged with O-137) but not the AVR-Pita form from G-198 (which in planta results in disease susceptibility phenotype when Yashiro-mochi is challenged with G-198). In addition, the results described in Table 5 identified two Pi-ta constructs encoding Pi-ta proteins with amino acid 918 changed to either M or C that recognized both avirulent (AVR-Pita from O-137) and virulent (avr-pita from G-198) AVR-Pita gene products. As can be seen from the table, M918 Pi-ta gave rise to multiple GUS loci when there was no AVR-Pita gene co-bombarded with the other constructs, indicating that by itself, M918 is not able to cause the hypersensitive response; this indicated that the absence of GUS loci observed when AVR-Pita gene was present was indeed due to productive recognition between AVR-Pita and Pi-ta gene products and not from other reasons like autoactivation of the Pi-ta protein leading to the hypersensitive response. Another form with an I at position 918 had switched specificity relative to the Pi-ta protein from Yashiro-mochi (A918) since it only recognized the virulent G-198 allele but not the O-137 allele. Other constructs encoding proteins containing R, K, N, L, and Q at position 918 also resulted in recognition of the G-198 allele.

These data suggest that it is possible to alter the range of AVR-Pita alleles that Pi-ta can recognize by changing the amino acid at position 918 of the Pi-ta protein. Consequently, transgenic rice plants that are able to recognize *M. grisea* strain G-198 and/or other strains containing an AVR-Pita gene substantially similar to that found in SEQ ID NO:4 and undergo an HR or disease resistance response may be obtained by transforming rice with a modified Pi-ta nucleic acid fragment which encodes a Pi-ta protein that has at position 918 an amino acid selected from the grout, consisting of M, C, I, R, K, N, L and Q.

Additionally, modified Pi-ta nucleic acid fragments which encode a Pi-ta protein that has at position 918 an amino acid selected from the group consisting of M, C, I, R, K, N, L and Q, may be introduced into rice varieties that already have a functional Pi-ta (A918), resulting in lines which can mount a disease resistance response to a broader range of *M. grisea* strains.

Example 6

Construction of Chimeric Genes Encoding Modified Pi-ta Proteins for Stable Rice Transformation Plasmids comprising nucleic acid fragments encoding the altered forms of Pi-ta identified in Example 5 were constructed using vector pCB1926 and thus do not have a terminator sequence. For stable rice transformation, the vector pCB2022 is the preferred Pi-ta format for a Pi-ta nucleic acid fragment as in addition to the 2425 bp of Pi-ta native promoter sequence and 2784 bp of Pi-ta coding sequence it contains an In2-1 terminator sequence (SEQ ID NO:60). Plasmid pCB2022 has been deposited with the ATCC. To make the precursor plasmid pCB2021, the entire 5222 bp EcoRI-HindIII Pi-ta nucleic acid fragment was excised from plasmid pCB1926 using a partial digest (as there is a second EcoRI site within the Pi-ta cDNA nucleic acid fragment) and cloned into the same sites of plasmid Litmus 28a (New England Biolabs). Plasmid pCB2021 was then digested with AgeI and KpnI and a 501 bp AgeI-KpnI In2-1 terminator nucleic acid fragment was cloned into the same sites to create pCB2022. The In2-1 terminator sequence may be amplified from plasmids containing In2-1 terminator sequence (e.g., pJE514, pJE516, and pTDS136 disclosed in U.S. Pat. No. 5,364,780, the disclosure of which is hereby incorporated by reference) using primers GB188 (SEQ ID NO:54) and GB189 (SEQ ID NO:55), then digested with AgeI and KpnI.

GB188: 5'-GCCGACCGGTAGATCTGACAAAGCAG CATTAG-3' (SEQ ID NO:54)

GB189: 5'-CGGCGGTACCGCTCTCTCTCTCCCCT TGC-3' (SEQ ID NO:55)

Modified Pi-ta nucleic acid fragments identified in Example 5 which encode Pi-ta protein wherein the amino acid alteration at position 918 is selected from the group consisting of M, C, I, R, K, N, L and Q, and are suitable for stable rice transformation can be made in a two-stage cloning step. A 2.1 kb BamHI-HindIII fragment from pCB2176, pCB2180, pCB2177, pCB2173, pCB2174, pCB2175, pCB2185, or pCB2183 can be cloned into vector pCB2021 to replace the corresponding fragment from the wild-type Pi-ta nucleic acid fragment present in pCB2021. Then the 501 bp AgeI-KpnI In2-1 terminator nucleic acid fragment can be excised from vector pCB2022 by digesting with AgeI and KpnI and cloned into the same sites on the new vector that has also been digested with AgeI and KpnI. These new vectors can then be used in stable rice transformation as described in Example 7 below.

Example 7

Testing Chimeric Genes Encoding Modified Pi-ta Proteins from Example 6 by Stable Rice Transformation The bacterial hygromycin B phosphotransferase (Hpt II) gene from *Streptomyces hygroscopicus* that confers resistance to the antibiotic can be used as the selectable marker for rice transformation. In the vector that could be used, pML 18, the Hpt II gene has been engineered with the 35S promoter from Cauliflower Mosaic Virus and the termination and polyadenylation signals from the octopine synthase gene of *Agrobacterium tumefaciens*. pML 18 is described in WO 97/47731, which was published on Dec. 18, 1997, the disclosure of which is hereby incorporated by reference.

Embryogenic callus cultures derived from the scutellum of germinating Nipponbare seeds can serve as source material for transformation experiments. This material is generated by germinating sterile rice seeds on a callus initiation media (MS salts, Nitsch and Nitsch vitamins, 1.0 mg/l 2,4-D and 10 μM $AgNO_3$) in the dark at 27–28° C. Embryogenic callus proliferating from the scutellum of the embryos are then transferred to CM media (N6 salts, Nitsch and Nitsch vitamins, 1 mg/l 2,4-D, Chu et al., 1985, *Sci. Sinica* 18: 659–668). Callus cultures can be maintained on CM by routine sub-culture at two week intervals and used for transformation within 10 weeks of initiation.

Callus can be prepared for transformation by subculturing 0.5–1.0 mm pieces approximately 1 mm apart, arranged in a circular area of about 4 cm in diameter, in the center of a circle of Whatman #541 paper placed on CM media. The plates with callus are then incubated in the dark at 27–28° C. for 3–5 days. Prior to bombardment, the filters with callus are transferred to CM supplemented with 0.25 M mannitol and 0.25 M sorbitol for 3 hr. in the dark. The petri dish lids are then left ajar for 20–45 minutes in a sterile hood to allow moisture on tissue to dissipate.

Circular plasmid DNA from two different plasmids, for example, pML18 containing the selectable marker for rice transformation and a vector containing the modified Pi-ta nucleic acid fragment, can be co-precipitated onto the surface of gold particles. To accomplish this, a total of 10 μg of DNA at a 2:1 ratio of trait:selectable marker DNAs are added to 50 μl aliquot of gold particles that have been resuspended at a concentration of 60 mg $ml^{-1}$. Calcium chloride (50 μl of a 2.5 M solution) and spermidine (20 μl of a 0.1 M solution) are then added to the gold-DNA suspension and the tube would be vortexed for 3 min. The gold particles are centrifuged in a microfuge for 1 sec and the supernatant removed. The gold particles are then washed twice with 1 ml of absolute ethanol and then resuspended in 50 μl of absolute ethanol and sonicated (bath sonicator) for one second to disperse the gold particles. The gold suspension is then incubated at −70° C. for five minutes and sonicated (bath sonicator) if needed to disperse the particles. Six μl of the DNA-coated gold particles can then be loaded onto mylar macrocarrier disks and the ethanol allowed to evaporate.

At the end of the drying period, a petri dish containing the tissue is placed in the chamber of the PDS-1000/He. The air in the chamber is then evacuated to a vacuum of 28–29 inches Hg. The macrocarrier accelerated with a helium shock wave using a rupture membrane that bursts when the He pressure in the shock tube reaches 1080–1100 psi. The tissue is placed approximately 8 cm from the stopping screen and the callus bombarded two times. Five to seven plates of tissue are bombarded in this way with the DNA-coated gold particles. Following bombardment, the callus tissue is transferred to CM media without supplemental sorbitol or mannitol.

Within 3–5 days after bombardment the callus tissue is transferred to SM media (CM medium containing 50 mg/I hygromycin). To accomplish this, callus tissue is transferred from plates to sterile 50 ml conical tubes and weighed. Molten top-agar at 40° C. can be added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates can be incubated in the dark for 4 weeks at 27–28° C. After 4 weeks, transgenic callus events are identified, transferred to fresh SM plates and grown for an additional 2 weeks in the dark at 27–28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus can be transferred to RM2 media (MS salts, Nitsch and Nitsch vitamins, 3% sucrose, 0.4% gelrite+50 ppm hyg B) and placed under cool white light (~40 $\mu Em^{-2}s^{-1}$) with a 12 hr photoperiod at 25° C. and 30–40% humidity. After 2–4 weeks in the light, callus begins to organize, and form shoots. Shoots are then removed from surrounding callus/media and gently transferred to RM3 media (½×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2–3 weeks, when sufficient root and shoot growth had occurred. Plants can be grown using a 12 hr/12 hr light/dark cycle using ~30/18° C. day/night temperature regimen.

What is claimed is:

1. An isolated nucleic acid fragment comprising a nucleic acid sequence encoding an altered Pi-ta resistance polypeptide selected from the group consisting of:

(a) a nucleic acid sequence having at least 90% sequence identity when compared to nucleotides 2426–5212 of the nucleic acid sequence of SEQ ID NO:57, wherein the altered Pi-ta resistance polypeptide has an amino acid substitution for alanine at position 918 and confers resistance in a plant transformed therewith against the fungus Magnaporthe comprising in its genome one or more virulent and/or avirulent AVR-Pita alleles, and (b) a nucleic acid sequence encoding an amino acid sequence as set forth in SEQ ID NO:58 wherein the amino acid sequence has a single amino acid substitution at position 918 which confers resistance in a plant transformed therewith against the fungus Magnaporthe comprising in its genome one or more virulent and/or avirulent AVR-Pita alleles.

2. The isolated nucleic acid fragment of claim 1 wherein the amino acid at position 918 is selected from the group consisting of M, C, I, R, K, N, L and Q.

3. A chimeric gene comprising the nucleic acid fragment of claim 1 or 2 operably linked to at least one regulatory sequence.

4. A plant comprising in its genome the chimeric gene of claim 3.

5. The plant of claim 4 wherein said plant is selected from the group consisting of rice, wheat, barley, corn, finger millet sorghum, and pearl millet.

6. A transformed seed of the plant of claim 4.

7. A method of conferring resistance in a plant against the fungus Magnaporthe comprising in its genome virulent and/or avirulent AVR-Pita alleles which comprises wherein said plant has increased resistance against the fungus Magnaporthe comprising in its genome one or more virulent and/or avirulent AVR-Pita alleles as compared to an untransformed plant.

8. A transformed seed of the plant of claim 5.

* * * * *

UNITED STATES PATENT AND TRADEMARK OFFICE
CERTIFICATE OF CORRECTION

PATENT NO.         : 6,743,969 B2
APPLICATION NO. : 09/993170
DATED                  : June 1, 2004
INVENTOR(S)        : Gregory T. Bryan and Barbara Valent It is certified that error appears in the above-identified patent and that said Letters Patent is hereby corrected as shown below:

Title page of patent, (56) OTHER PUBLICATIONS section, first reference listed: please delete "Lazer" and insert therefor --Lazar--.

Page 2 of patent, OTHER PUBLICATIONS section, Traut reference listed in first column: please delete "Peptides" and insert therefor --Peptide--.

Page 2 of patent, OTHER PUBLICATIONS section, Nakamura reference listed in second column, please delete "Representice" and insert therefor --Representative--.

Page 2 of patent, OTHER PUBLICATIONS section, Leung reference listed in second column, please delete "Leunget." and insert therefor --Leung et.--.

Page 2 of patent, OTHER PUBLICATIONS section, Mascarenhas reference listed in second column, after "Plant Molecular" insert the word --Biology--.

Page 2 of patent, OTHER PUBLICATIONS section, Jones reference listed in first column, please delete "Transposen" and insert therefor --Transposon--.

Page 2 of patent, OTHER PUBLICATIONS section, Sasaki reference listed in first column, alter "vol. 1:81- 85," please insert --1922--.

Page 2 of patent, OTHER PUBLICATIONS section, MacKill reference listed in first column, please delete "Blasr" and insert therefor --Blast--.

Page 2 of patent, OTHER PUBLICATIONS section, Yue reference listed in second column, please delete "Yue" and insert therefor --Yu--; please delete "Phytopathological and insert therefor --Phytopathology--.

Page 2 of patent, OTHER PUBLICATIONS section, Yu reference listed in second column, please delete "Link Age" and insert therefor --Linkage--.

Page 2 of patent, OTHER PUBLICATIONS section, Wang reference listed in second column, please delete "PF" and insert therefor --of--.

Page 3 of patent, OTHER PUBLICATIONS section, Richards reference listed in first column, please delete "Ericd" and insert therefor –Eric–; please delete "Col." and insert therefor --Vol.--.

Page 3 of patent, OTHER PUBLICATIONS section, Murashlge reference listed in second column, please delete "Physoil." and insert therefor --Physiol.--.

Page 3 of patent, OTHER PUBLICATIONS section, Jefferson reference listed in second column, please delete "Chimericf GNES" and insert therefor --Chimeric Genes--.

Page 3 of patent, OTHER PUBLICATIONS section, Jones reference listed in second column, please delete "Embro" and insert therefor --EMBO--.

UNITED STATES PATENT AND TRADEMARK OFFICE
CERTIFICATE OF CORRECTION

PATENT NO.         : 6,743,969 B2
APPLICATION NO. : 09/993170
DATED              : June 1, 2004
INVENTOR(S)        : Gregory T. Bryan and Barbara Valent It is certified that error appears in the above-identified patent and that said Letters Patent is hereby corrected as shown below:

Page 3 of patent, OTHER PUBLICATIONS section, MacKill reference listed in first column, please delete "Blasr" and insert therefor --Blast--.
     Column 89, claim 7, line 3 of patent, after the word "comprises", insert therefor --transforming a plant with the chimeric gene of claim 3;--.

Signed and Sealed this

Fourteenth Day of November, 2006

JON W. DUDAS
*Director of the United States Patent and Trademark Office*

SEQUENCE LISTING

<160> NUMBER OF SEQ ID NOS: 60

<210> SEQ ID NO 1
<211> LENGTH: 4119
<212> TYPE: DNA
<213> ORGANISM: Artificial Sequence
<220> FEATURE:
<223> OTHER INFORMATION: Description of Artificial Sequence:Plasmid

<400> SEQUENCE: 1

| | | | | | |
|---|---|---|---|---|---|
| cacctaaatt | gtaagcgtta | atattttgtt | aaaattcgcg | ttaaattttt | gttaaatcag | 60 |
| ctcatttttt | aaccaatagg | ccgaaatcgg | caaaatccct | tataaatcaa | aagaatagac | 120 |
| cgagataggg | ttgagtgttg | ttccagtttg | gaacaagagt | ccactattaa | agaacgtgga | 180 |
| ctccaacgtc | aaagggcgaa | aaaccgtcta | tcagggcgat | ggcccactac | gtgaaccatc | 240 |
| accctaatca | agttttttgg | ggtcgaggtg | ccgtaaagca | ctaaatcgga | accctaaagg | 300 |
| gagcccccga | tttagagctt | gacggggaaa | gccggcgaac | gtggcgagaa | aggaagggaa | 360 |
| gaaagcgaaa | ggagcgggcg | ctagggcgct | ggcaagtgta | gcggtcacgc | tgcgcgtaac | 420 |
| caccacaccc | gccgcgctta | atgcgccgct | acagggcgcg | tcccattcgc | cattcaggct | 480 |
| gcgcaactgt | tgggaagggc | gatcggtgcg | ggcctcttcg | ctattacgcc | agctggcgaa | 540 |
| agggggatgt | gctgcaaggc | gattaagttg | ggtaacgcca | gggttttccc | agtcacgacg | 600 |
| ttgtaaaacg | acggccagtg | aattgtaata | cgactcacta | tagggcgaat | tgggtaccgg | 660 |
| gccccccctc | gaggtcgatc | cgagggtagg | tctaggggcc | tgatcctcac | aatattttg | 720 |
| taaatttcaa | aagtcaggga | gcatgaatta | tgtagttatt | aataatatgg | gcccaactct | 780 |
| taccttatat | aaaattgtgg | atgatatact | aataaaagtg | gacctaatta | cctgcataat | 840 |
| aatgcagata | attaacacta | gcaaaatata | attcgataat | attattaatg | ctaaataacg | 900 |
| cattaataaa | ccaaataagt | tttacatctt | cctaaagctt | tgaaaaagt | caagctgaaa | 960 |
| taataaataa | gttggcgttg | ttataaaatc | gacccgtttc | cgcctttatt | ggtttaattc | 1020 |
| ggatagagaa | cattttgctt | ataattccaa | acatacaaac | aattatccac | tgactgaaaa | 1080 |
| tcgacagttt | tgtttgcaca | atcaacatta | taattacaat | taaaaacttc | tgcacaatta | 1140 |
| acattatttt | tgcatcgatg | ctttttttatt | cattattttt | ttttcacacc | gttgcgattt | 1200 |
| cggccttcac | caacattggc | acctttttcac | acccagttta | cgattacaat | ccaattccaa | 1260 |
| accatatcca | cggagattta | aaaaggcggg | cttatattga | acgctattcc | caatgttcag | 1320 |
| attcgcaggc | ctccgaaatt | cgtgccgcgc | taaaaagttg | tgccgagctc | gcctcgtggg | 1380 |
| gctatcacgc | cgttaaaaat | gacaatcggt | tatttagatt | aatctttaaa | actgacagca | 1440 |
| cagatattca | aaactgggtt | caaagaatt | ttaacgaaat | ttacaaggaa | tgtaacaggg | 1500 |
| acgcggacga | aatttctcta | acctgccacg | ataaaaatgt | ttatacgtgc | gtccgagaag | 1560 |
| gagttcataa | tttggcgtat | gcacttatta | acgaaaaaga | aattgttata | tgccctcctt | 1620 |
| tcttcaacaa | ccccgtaaac | agcagggaaa | ttactgccgg | taaccaagat | acagttatat | 1680 |
| tacatgaaat | ggtgcatata | atttaaaag | agtggaaaga | ttatggttac | gaatgggatg | 1740 |
| ggattcacaa | attggatagt | acagaaagta | ttaaaaaccc | cgacagttat | gctatttttg | 1800 |
| cacaatgtgc | acgttataaa | tattgttaaa | taacgttagt | gttggaatgg | agggaatcgc | 1860 |
| ggtcaatcta | acaatagagg | gatccactag | ttctagagcg | gccgccaccg | cggtggagct | 1920 |
| ccagcttttg | ttccctttag | tgagggttaa | tttcgagctt | ggcgtaatca | tggtcatagc | 1980 |

-continued

```
tgtttcctgt gtgaaattgt tatccgctca caattccaca caacatacga gccggaagca    2040
taaagtgtaa agcctggggt gcctaatgag tgagctaact cacattaatt gcgttgcgct    2100
cactgcccgc tttccagtcg ggaaacctgt cgtgccagct gcattaatga atcggccaac    2160
gcgcggggag aggcggtttg cgtattgggc gctcttccgc ttcctcgctc actgactcgc    2220
tgcgctcggt cgttcggctg cggcgagcgg tatcagctca ctcaaaggcg gtaatacggt    2280
tatccacaga atcaggggat aacgcaggaa agaacatgtg agcaaaaggc cagcaaaagg    2340
ccaggaaccg taaaaaggcc gcgttgctgg cgttttttcca taggctccgc cccctgacg    2400 agcatcacaa aaatcgacgc tcaagtcaga ggtggcgaaa cccgacagga ctataaagat    2460
accaggcgtt tccccctgga agctcccctcg tgcgctctcc tgttccgacc ctgccgctta    2520
ccggatacct gtccgccttt ctcccttcgg gaagcgtggc gctttctcat agctcacgct    2580
gtaggtatct cagttcggtg taggtcgttc gctccaagct gggctgtgtg cacgaacccc    2640
ccgttcagcc cgaccgctgc gccttatccg gtaactatcg tcttgagtcc aacccggtaa    2700
gacacgactt atcgccactg gcagcagcca ctggtaacag gattagcaga gcgaggtatg    2760
taggcggtgc tacagagttc ttgaagtggt ggcctaacta cggctacact agaaggacag    2820
tatttggtat ctgcgctctg ctgaagccag ttaccttcgg aaaaagagtt ggtagctctt    2880
gatccggcaa acaaaccacc gctggtagcg gtggtttttt tgtttgcaag cagcagatta    2940
cgcgcagaaa aaaggatct caagaagatc ctttgatctt ttctacgggg tctgacgctc    3000
agtggaacga aaactcacgt taagggattt tggtcatgag attatcaaaa aggatcttca    3060
cctagatcct tttaaattaa aaatgaagtt ttaaatcaat ctaaagtata tatgagtaaa    3120
cttggtctga cagttaccaa tgcttaatca gtgaggcacc tatctcagcg atctgtctat    3180
ttcgttcatc catagttgcc tgactccccg tcgtgtagat aactacgata cgggagggct    3240
taccatctgg ccccagtgct gcaatgatac cgcgagaccc acgctcaccg gctccagatt    3300
tatcagcaat aaaccagcca gccggaaggg ccgagcgcag aagtggtcct gcaactttat    3360
ccgcctccat ccagtctatt aattgttgcc gggaagctag agtaagtagt tcgccagtta    3420
atagtttgcg caacgttgtt gccattgcta caggcatcgt ggtgtcacgc tcgtcgtttg    3480
gtatggcttc attcagctcc ggttcccaac gatcaaggcg agttacatga tcccccatgt    3540
tgtgcaaaaa agcggttagc tccttcggtc ctccgatcgt tgtcagaagt aagttggccg    3600
cagtgttatc actcatggtt atggcagcac tgcataattc tcttactgtc atgccatccg    3660
taagatgctt ttctgtgact ggtgagtact caaccaagtc attctgagaa tagtgtatgc    3720
ggcgaccgag ttgctcttgc ccggcgtcaa tacgggataa taccgcgcca catagcagaa    3780
ctttaaaagt gctcatcatt ggaaaacgtt cttcggggcg aaaactctca aggatcttac    3840
cgctgttgag atccagttcg atgtaaccca ctcgtgcacc caactgatct tcagcatctt    3900
ttactttcac cagcgtttct gggtgagcaa aacaggaag gcaaaatgcc gcaaaaaagg    3960
gaataagggc gacacggaaa tgttgaatac tcatactctt cctttttcaa tattattgaa    4020
gcatttatca gggttattgt ctcatgagcg gatacatatt tgaatgtatt tagaaaaata    4080
aacaaatagg ggttccgcgc acatttcccc gaaaagtgc                          4119
```

<210> SEQ ID NO 2
<211> LENGTH: 672
<212> TYPE: DNA
<213> ORGANISM: Magnaporthe grisea

<400> SEQUENCE: 2

```
atgctttttt attcattatt ttttttttcac accgttgcga tttcggcctt caccaacatt      60
ggcacctttt cacacccagt ttacgattac aatccaattc caaaccatat ccacggagat     120
ttaaaaaggc gggcttatat tgaacgctat tcccaatgtt cagattcgca ggcctccgaa     180
attcgtgccg cgctaaaaag ttgtgccgag ctcgcctcgt ggggctatca cgccgttaaa     240
aatgacaatc ggttatttag attaatcttt aaaactgaca gcacagatat tcaaaactgg     300
gttcaaaaga atttttaacga aatttacaag gaatgtaaca gggacgcgga cgaaatttct     360
ctaacctgcc acgataaaaa tgtttatacg tgcgtccgag aaggagttca taatttggcg     420
tatgcactta ttaacgaaaa agaaattgtt atatgccctc ctttcttcaa caaccccgta     480
aacagcaggg aaattactgc cggtaaccaa gatacagtta tattacatga atggtgcat      540
ataattttaa aagagtggaa agattatggt tacgaatggg atgggattca caaattggat     600
agtacagaaa gtattaaaaa ccccgacagt tatgctattt ttgcacaatg tgcacgttat     660
aaatattgtt aa                                                         672
```

<210> SEQ ID NO 3
<211> LENGTH: 223
<212> TYPE: PRT
<213> ORGANISM: Magnaporthe grisea

<400> SEQUENCE: 3

```
Met Leu Phe Tyr Ser Leu Phe Phe His Thr Val Ala Ile Ser Ala
  1               5                  10                  15

Phe Thr Asn Ile Gly Thr Phe Ser His Pro Val Tyr Asp Tyr Asn Pro
                 20                  25                  30

Ile Pro Asn His Ile His Gly Asp Leu Lys Arg Arg Ala Tyr Ile Glu
         35                  40                  45

Arg Tyr Ser Gln Cys Ser Asp Ser Gln Ala Ser Glu Ile Arg Ala Ala
     50                  55                  60

Leu Lys Ser Cys Ala Glu Leu Ala Ser Trp Gly Tyr His Ala Val Lys
 65                  70                  75                  80

Asn Asp Asn Arg Leu Phe Arg Leu Ile Phe Lys Thr Asp Ser Thr Asp
                 85                  90                  95

Ile Gln Asn Trp Val Gln Lys Asn Phe Asn Glu Ile Tyr Lys Glu Cys
            100                 105                 110

Asn Arg Asp Ala Asp Glu Ile Ser Leu Thr Cys His Asp Lys Asn Val
        115                 120                 125

Tyr Thr Cys Val Arg Glu Gly Val His Asn Leu Ala Tyr Ala Leu Ile
    130                 135                 140

Asn Glu Lys Glu Ile Val Ile Cys Pro Pro Phe Phe Asn Asn Pro Val
145                 150                 155                 160

Asn Ser Arg Glu Ile Thr Ala Gly Asn Gln Asp Thr Val Ile Leu His
                165                 170                 175

Glu Met Val His Ile Ile Leu Lys Glu Trp Lys Asp Tyr Gly Tyr Glu
            180                 185                 190

Trp Asp Gly Ile His Lys Leu Asp Ser Thr Glu Ser Ile Lys Asn Pro
        195                 200                 205

Asp Ser Tyr Ala Ile Phe Ala Gln Cys Ala Arg Tyr Lys Tyr Cys
    210                 215                 220
```

<210> SEQ ID NO 4
<211> LENGTH: 788

<212> TYPE: DNA
<213> ORGANISM: Magnaporthe grisea

<400> SEQUENCE: 4

```
ttatttttat cgatatgctt tttgattcat tattttttt tcacaccgtt gcgatttcgg      60
cctgcaccaa cattggcacc ttttcacacc cagtttacga ttacaatcca attccaaacc    120
atatccacgg agatttaaaa aggcgggctt atattga Asp Ser Tyr Ala Ile Phe Ala Gln Cys Ala Arg Tyr Lys Tyr Cys
        210                 215                 220

<210> SEQ ID NO 6
<211> LENGTH: 672
<212> TYPE: DNA
<213> ORGANISM: Magnaporthe grisea

<400> SEQUENCE: 6 atgcttttt  attcattatt  ttttttcac  accgttgcga  tttcggcctt  caccaacatt      60 ggcaccttt  cacacccagt  ttacgattac  aatccaattc  caaaccatat  ccacggagat     120
ttaaaaaggc  gggcttatat  tgaacgctat  tcccaatgtt  cagattcgca  ggcctccgaa    180
attcgtgccg  cgctaaaaag  ttgcgccgag  ctcgcctcgt  ggggctatca  cgccgttaaa    240
agtaacaatc  ggttatttaa  attaatcttt  aaaactgaca  gcacagatat  tcaaaactgg    300
gttcaaaata  attttaacga  aatttacaag  gaatgtaaca  gggacgcgga  cgaaatttct    360
ctaacctgcc  acgataaaaa  tgtttatacg  tgcgtccgag  aaggagttca  taatttggcg    420
tatgcactta  ttaacgaaaa  agaaattgtt  atatgccctc  ctttcttcaa  caaccccgta    480
aacagcaggg  aaattactgc  cggtaaccaa  gatacaatta  tattacatga  aatggtgcat    540
ataattttaa  aagagtggaa  agattatggt  tgcgaatggg  atgggattca  caaattggat    600
agtacagaaa  gtattaaaaa  ccccgacagt  tatgctattt  ttgcacaatg  tgcacgttat    660
aaatattgtt  aa                                                            672

<210> SEQ ID NO 7
<211> LENGTH: 223
<212> TYPE: PRT
<213> ORGANISM: Magnaporthe grisea

<400> SEQUENCE: 7

Met Leu Phe Tyr Ser Leu Phe Phe His Thr Val Ala Ile Ser Ala
  1               5                  10                  15

Phe Thr Asn Ile Gly Thr Phe Ser His Pro Val Tyr Asp Tyr Asn Pro
             20                  25                  30

Ile Pro Asn His Ile His Gly Asp Leu Lys Arg Arg Ala Tyr Ile Glu
         35                  40                  45

Arg Tyr Ser Gln Cys Ser Asp Ser Gln Ala Ser Glu Ile Arg Ala Ala
     50                  55                  60

Leu Lys Ser Cys Ala Glu Leu Ala Ser Trp Gly Tyr His Ala Val Lys
 65                  70                  75                  80

Ser Asn Asn Arg Leu Phe Lys Leu Ile Phe Lys Thr Asp Ser Thr Asp
                 85                  90                  95

Ile Gln Asn Trp Val Gln Asn Asn Phe Asn Glu Ile Tyr Lys Glu Cys
            100                 105                 110

Asn Arg Asp Ala Asp Glu Ile Ser Leu Thr Cys His Asp Lys Asn Val
        115                 120                 125

Tyr Thr Cys Val Arg Glu Gly Val His Asn Leu Ala Tyr Ala Leu Ile
    130                 135                 140

Asn Glu Lys Glu Ile Val Ile Cys Pro Pro Phe Phe Asn Asn Pro Val
145                 150                 155                 160

Asn Ser Arg Glu Ile Thr Ala Gly Asn Gln Asp Thr Ile Ile Leu His
                165                 170                 175

Glu Met Val His Ile Ile Leu Lys Glu Trp Lys Asp Tyr Gly Cys Glu
            180                 185                 190

-continued

```
Trp Asp Gly Ile His Lys Leu Asp Ser Thr Glu Ser Ile Lys Asn Pro
        195                 200                 205

Asp Ser Tyr Ala Ile Phe Ala Gln Cys Ala Arg Tyr Lys Tyr Cys
    210                 215                 220
```

<210> SEQ ID NO 8
<211> LENGTH: 884
<212> TYPE: DNA
<213> ORGANISM: Magnaporthe grisea

<400> SEQUENCE: 8

```
atgctttttt attcattgtt atttttattt cacaccgttg cgatttcggc cttcaccaac     60
attggcacct tttcacaccc agtttacgat tacaatccaa ttccaaacca tatccacgga    120
gatttaaaaa ggcgggctta tattgaacgc tattcccaat gttcagattc gcaggcctcc    180
gaaattcgtg ccgcgctaaa aaggtaaatt gaaactcttt aaaacaaatt cggaaaacaa    240
tgttaaatat tttgtttagt tgcgccgagc tcgcctcgtg gggctatcac gccgttaaaa    300
gtgacaatcg gttatttaaa ttaatcttta aaactgacag cacagatatt caaaactggg    360
ttcaaaataa ttttaacgaa atttacaagg aatgtaacag ggacgcggac gaaatttctc    420
taacctgcca cgataaaaat gtttatacgt gcgtccgaga agaagttcat aatttggcgt    480
atgcacttat taacgaaaaa gaaattgtta tatgccctcc tttcttcaac aaccccgtaa    540
acagcaggga aattactgcc ggtaaccaag atacaattat attacatgaa atggtgcata    600
taattttaag taagtttgct tttacaaatt gataaaacat ttacaaaagt ttatttataa    660
aaattttcaa aaactaaaaa ttcaaatttt tatttagaag agtggaaaga ttatggttac    720
gaatgggatg ggattcacaa gtaagttgtc gaaaaacaaa atgctgaatg ttgttttata    780
ttgataaatt ctaattaata ttaagattgg atagtacaga aagtattaaa aaccccgaca    840
gttatgctat ttttgcacaa tgtgcacgtt ataaatattg ttaa                     884
```

<210> SEQ ID NO 9
<211> LENGTH: 675
<212> TYPE: DNA
<213> ORGANISM: Magnaporthe grisea

<400> SEQUENCE: 9

```
atgctttttt attcattgtt atttttattt cacaccgttg cgatttcggc cttcaccaac     60
attggcacct tttcacaccc agtttacgat tacaatccaa ttccaaacca tatccacgga    120
gatttaaaaa ggcgggctta tattgaacgc tattcccaat gttcagattc gcaggcctcc    180
gaaattcgtg ccgcgctaaa aagttgcgcc gagctcgcct cgtggggcta tcacgccgtt    240
aaaagtgaca atcggttatt taaattaatc tttaaaactg acagcacaga tattcaaaac    300
tgggttcaaa ataattttaa cgaaatttac aaggaatgta acagggacgc ggacgaaatt    360
tctctaacct gccacgataa aaatgtttat acgtgcgtcc gagaagaagt tcataatttg    420
gcgtatgcac ttattaacga aaaagaaatt gttatatgcc ctcctttctt caacaacccc    480
gtaaacagca gggaaattac tgccggtaac caagatacaa ttatattaca tgaaatggtg    540
catataattt taaaagagtg gaaagattat ggttacgaat gggatgggat tcacaaattg    600
gatagtacag aaagtattaa aaaccccgac agttatgcta tttttgcaca atgtgcacgt    660
tataaatatt gttaa                                                     675
```

<210> SEQ ID NO 10

<211> LENGTH: 224
<212> TYPE: PRT
<213> ORGANISM: Magnaporthe grisea

<400> SEQUENCE: 10

```
Met Leu Phe Tyr Ser Leu Leu Phe Leu Phe His Thr Val Ala Ile Ser
 1               5                  10                  15
Ala Phe Thr Asn Ile Gly Thr Phe Ser His Pro Val Tyr Asp Tyr Asn
             20                  25                  30
Pro Ile Pro Asn His Ile His Gly Asp Leu Lys Arg Arg Ala Tyr Ile
         35                  40                  45
Glu Arg Tyr Ser Gln Cys

-continued

```
gaatgggatg ggattcacaa gtaagttgtc gaaaaacaaa atgctgaatg ttgtttata      780 ttgataaatt ctaattaata ttaagattgg atagtacaga aagtattaaa aaccccgaca      840
gttatgctat ttttgcacaa tgtgcacgtt ataaatattg ttaa                       884
```

<210> SEQ ID NO 12
<211> LENGTH: 675
<212> TYPE: DNA
<213> ORGANISM: Magnaporthe grisea

<400> SEQUENCE: 12

```
atgctttttt attcattgtt attttattt cacaccgttg cgatttcggc cttcaccaac       60
attggcacct tttcacaccc agtttacgat tacaatccaa ttccaaacca tatccacgga      120
gatttaaaaa ggcgggctta tattgaacgc tattcccaat gttcagattc gcaggcctcc      180
gaaattcgtg ccgcgctaaa aagttgcgcc gagctcgcct cgtggggcta tcacgccgtt      240
aaaagtaaca atcggttatt taaattaatc tttaaaactg acagcacaga tattcaaaac      300
tgggttcaaa ataattttaa cgaaatttac aaggaatgta acagggacgc ggacgaaatt      360
tctctaacct gccacgataa aaatgtttat acgtgcgtcc gagaagaagt tcataatttg      420
gcgtatgcac ttattaacga aaagaaatt gttatatgcc ctccttctct caacaacccc      480
gtaaacagca gggaaattac tgccggtaac caagatacaa ttatattaca tgaaatggtg      540
catataattt taaagagtg gaaagattat ggttgcgaat gggatgggat tcacaaattg      600
gatagtacag aaagtattaa aaaccccgac agttatgcta ttttgcaca atgtgcacgt      660 tataaatatt gttaa                                                        675
```

<210> SEQ ID NO 13
<211> LENGTH: 224
<212> TYPE: PRT
<213> ORGANISM: Magnaporthe grisea

<400> SEQUENCE: 13

```
Met Leu Phe Tyr Ser Leu Leu Phe Leu Phe His Thr Val Ala Ile Ser
  1               5                  10                  15

Ala Phe Thr Asn Ile Gly Thr Phe Ser His Pro Val Tyr Asp Tyr Asn
             20                  25                  30

Pro Ile Pro Asn His Ile His Gly Asp Leu Lys Arg Arg Ala Tyr Ile
         35                  40                  45

Glu Arg Tyr Ser Gln Cys Ser Asp Ser Gln Ala Ser Glu Ile Arg Ala
     50                  55                  60

Ala Leu Lys Ser Cys Ala Glu Leu Ala Ser Trp Gly Tyr His Ala Val
 65                  70                  75                  80

Lys Ser Asn Asn Arg Leu Phe Lys Leu Ile Phe Lys Thr Asp Ser Thr
                 85                  90                  95

Asp Ile Gln Asn Trp Val Gln Asn Asn Phe Asn Glu Ile Tyr Lys Glu
            100                 105                 110

Cys Asn Arg Asp Ala Asp Glu Ile Ser Leu Thr Cys His Asp Lys Asn
        115                 120                 125

Val Tyr Thr Cys Val Arg Glu Glu Val His Asn Leu Ala Tyr Ala Leu
    130                 135                 140

Ile Asn Glu Lys Glu Ile Val Ile Cys Pro Pro Phe Phe Asn Asn Pro
145                 150                 155                 160

Val Asn Ser Arg Glu Ile Thr Ala Gly Asn Gln Asp Thr Ile Ile Leu
                165                 170                 175
```

His Glu Met Val His Ile Ile Leu Lys Glu Trp Lys Asp Tyr Gly Cys
            180                 185                 190

Glu Trp Asp Gly Ile His Lys Leu Asp Ser Thr Glu Ser Ile Lys Asn
        195                 200                 205

Pro Asp Ser Tyr Ala Ile Phe Ala Gln Cys Ala Arg Tyr Lys Tyr Cys
    210                 215                 220

<210> SEQ ID NO 14
<211> LENGTH: 884
<212> TYPE: DNA
<213> ORGANISM: Magnaporthe grisea

<400> SEQUENCE: 14

| | | | | | |
|---|---|---|---|---|---|
| atgctttttt | attcatttat | attttatttt | cacaccgttg | caatttcggc | cttcaccaac | 60 |
| attggcacct | tttcataccc | agtttacatt | tacaatccaa | ttccaaacca | tatccacgga | 120 |
| gatttaaaaa | ggcgggctta | tattgaaccc | tattcccaat | gttcaaattc | gcaggactcc | 180 |
| gaaattcgtg | ccgcgctaaa | aagtaaatt | gaaattcttt | aagacaaatt | cggaaaacaa | 240 |
| tgttaaatat | tttgtttagt | tgtgccgaac | tcgcctcgtg | ggcctatcac | gccgttgaaa | 300 |
| atgacaatcg | gttatttgaa | ttgatttta | aaactgacag | cacaaatatt | aaaaactggg | 360 |
| ttcaaaataa | ttttaacgaa | attcacaagg | aatgtaacag | ggacgcggac | gaaatttctc | 420 |
| tatcctgcca | cgatacaagt | gtttatacgt | gcgtccgaga | aggagttcat | cttttgggct | 480 |
| atgcaaagat | gtacgaaaaa | caagttgttt | atgccctca | tttctttgat | caccccgtaa | 540 |
| acagcaggga | aatcactgcc | caaaaccaag | atacagttat | attgcatgaa | atgctgcata | 600 |
| taattctaag | taagtttgct | tttacaaatt | aataaaatct | ttacaaaagg | ttattcataa | 660 |
| atattttcaa | aaactaacaa | ttcaaatttt | tatttagatg | agtgggaaga | ttatggttac | 720 |
| gaatgggatg | ggattcacaa | gtaagttgtc | gaaaaacaaa | tttgctaaaa | ttattttata | 780 |
| ttgataaatt | ctaattaata | taagtttgg | atagtacaac | aagtattaaa | aaccccgaca | 840 |
| gctatgctat | ttttgcacaa | tgtgcacgtt | ataaatattg | ttaa | | 884 |

<210> SEQ ID NO 15
<211> LENGTH: 675
<212> TYPE: DNA
<213> ORGANISM: Magnaporthe grisea

<400> SEQUENCE: 15

| | | | | | |
|---|---|---|---|---|---|
| atgctttttt | attcatttat | attttatttt | cacaccgttg | caatttcggc | cttcaccaac | 60 |
| attggcacct | tttcataccc | agtttacatt | tacaatccaa | ttccaaacca | tatccacgga | 120 |
| gatttaaaaa | ggcgggctta | tattgaaccc | tattcccaat | gttcaaattc | gcaggactcc | 180 |
| gaaattcgtg | ccgcgctaaa | agttgtgcc | gaactcgcct | cgtgggccta | tcacgccgtt | 240 |
| gaaaatgaca | atcggttatt | tgaattgatt | tttaaaactg | acagcacaaa | tattaaaaac | 300 |
| tgggttcaaa | ataattttaa | cgaaattcac | aaggaatgta | acaggacgc | ggacgaaatt | 360 |
| tctctatcct | gccacgatac | aagtgtttat | acgtgcgtcc | gagaaggagt | tcatcttttg | 420 |
| ggctatgcaa | agatgtacga | aaaacaagtt | gttatgcc | ctcatttctt | tgatcacccc | 480 |
| gtaaacagca | gggaaatcac | tgcccaaaac | caagatacag | ttatattgca | tgaaatgctg | 540 |
| catataattc | taaatgagtg | ggaagattat | ggttacgaat | gggatgggat | tcacaatttg | 600 |
| gatagtacaa | caagtattaa | aaaccccgac | agctatgcta | ttttgcaca | atgtgcacgt | 660 |
| tataaatatt | gttaa | | | | | 675 |

<210> SEQ ID NO 16
<211> LENGTH: 224
<212> TYPE: PRT
<213> ORGANISM: Magnaporthe grisea

<400> SEQUENCE: 16

Met Leu Phe Tyr Ser Phe Ile Phe Tyr Phe His Thr Val Ala Ile Ser
 1               5                  10                  15

Ala Phe Thr Asn Ile Gly Thr Phe Ser Tyr Pro Val Tyr Ile Tyr Asn
             20                  25                  30

Pro Ile Pro Asn His Ile His Gly Asp Leu Lys Arg Arg Ala Tyr Ile
         35                  40                  45

Glu Pro Tyr Ser Gln Cys Ser Asn Ser Gln Asp Ser Glu Ile Arg Ala
     50                  55                  60

Ala Leu Lys Ser Cys Ala Glu Leu Ala Ser Trp Ala Tyr His Ala Val
 65                  70                  75                  80

Glu Asn Asp Asn Arg Leu Phe Glu Leu Ile Phe Lys Thr Asp Ser Thr
                 85                  90                  95

Asn Ile Lys Asn Trp Val Gln Asn Asn Phe Asn Glu Ile His Lys Glu
            100                 105                 110

Cys Asn Arg Asp Ala Asp Glu Ile Ser Leu Ser Cys His Asp Thr Ser
        115                 120                 125

Val Tyr Thr Cys Val Arg Glu Gly Val His Leu Leu Gly Tyr Ala Lys
    130                 135                 140

Met Tyr Glu Lys Gln Val Val Leu Cys Pro His Phe Phe Asp His Pro
145                 150                 155                 160

Val Asn Ser Arg Glu Ile Thr Ala Gln Asn Gln Asp Thr Val Ile Leu
                165                 170                 175

His Glu Met Leu His Ile Ile Leu Asn Glu Trp Glu Asp Tyr Gly Tyr
            180                 185                 190

Glu Trp Asp Gly Ile His Asn Leu Asp Ser Thr Thr Ser Ile Lys Asn
        195                 200                 205

Pro Asp Ser Tyr Ala Ile Phe Ala Gln Cys Ala Arg Tyr Lys Tyr Cys
    210                 215                 220

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 17
gatcgaatcg atatgctttt ttattcatta ttttttttc                              40

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 18
gatcgaggat ccccctctat tgttagattg acc                                    33

<210> SEQ ID NO 19

```
<211> LENGTH: 34
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 19
aagcatatcg ataaaaataa tgttaattgt gcag                              34

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 20
gccgagtcgt tctgaggg                                                18

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 21
gatcgaatcg atatgctttt ttattcattg ttatttttat ttc                    43

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 22
ccctgggatc caacactaac gttatttaac a                                 31

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 23
gccgcatcga tatgctttt tattcattta tatttta                            37

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 24
gccggcacgt gccatgattg aacgctattc ccaatg                            36

<210> SEQ ID NO 25
<211> LENGTH: 30
```

```
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 25
gccgggatcc ccctctattg ttagattgac                                    30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 26
acaacaagcc ggcacgtgcc atggaacgct                                    30

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 27 tccttctttta ggtaccgctc tctc                                         24

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 28
gggcttccat ggaacgctat tcccaatgtt cag                                33

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 29
cactaaggta ccttaacaat atttataacg tgcac                              35

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 30
ccattaagct tggtttcaaa caatc                                         25

<210> SEQ ID NO 31
<211> LENGTH: 20
<212> TYPE: DNA
```

```
<213> ORGANISM: Artificial Sequence
<220> FEATURE:
<223> OTHER INFORMATION: Description of Artificial Sequence:Synthetic
      Oligonucleotide

<400> SEQUENCE: 31
gtggcttcca ttgttggatc                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 32
caatgccgag tgtgcaaaga                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 33
caatgccgag tgtgcaaagg                                                    20

<210> SEQ ID NO 34
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 34
aggcgagtcg acgtttcaaa caatcatcaa gtcaggttga agatgcatct caggtaaaga       60
tagaagc                                                                  67

<210> SEQ ID NO 35
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 35
aggcgagtcg acgtttcaaa caatcatcaa gtcaggttga agatgcatat caggtaaaga       60
tagaagc                                                                  67

<210> SEQ ID NO 36
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 36
aggcgagtcg acgtttcaaa caatcatcaa gtcaggttga agatgcatcc taggtaaaga       60
tagaagc                                                                  67
```

<210> SEQ ID NO 37
<211> LENGTH: 67
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 37
aggcgagtcg acgtttcaaa caatcatcaa gtcaggttga agatgcatct taggtaaaga    60
tagaagc    67

<210> SEQ ID NO 38
<211> LENGTH: 67
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 38
aggcgagtcg acgtttcaaa caatcatcaa gtcaggttga agatgcatat taggtaaaga    60
tagaagc    67

<210> SEQ ID NO 39
<211> LENGTH: 67
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 39
aggcgagtcg acgtttcaaa caatcatcaa gtcaggttga agatgcatca taggtaaaga    60
tagaagc    67

<210> SEQ ID NO 40
<211> LENGTH: 67
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 40
aggcgagtcg acgtttcaaa caatcatcaa gtcaggttga agatgcataa taggtaaaga    60
tagaagc    67

<210> SEQ ID NO 41
<211> LENGTH: 67
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 41
aggcgagtcg acgtttcaaa caatcatcaa gtcaggttga agatgcattg taggtaaaga    60
tagaagc    67

<210> SEQ ID NO 42
<211> LENGTH: 67

<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 42
aggcgagtcg acgtttcaaa caatcatcaa gtcaggttga agatgcatcc aaggtaaaga      60
tagaagc      67

<210> SEQ ID NO 43
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 43
aggcgagtcg acgtttcaaa caatcatcaa gtcaggttga agatgcatac aaggtaaaga      60
tagaagc      67

<210> SEQ ID NO 44
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 44
aggcgagtcg acgtttcaaa caatcatcaa gtcaggttga agatgcatgt aaggtaaaga      60
tagaagc      67

<210> SEQ ID NO 45
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 45
aggcgagtcg acgtttcaaa caatcatcaa gtcaggttga agatgcatga aaggtaaaga      60
tagaagc      67

<210> SEQ ID NO 46
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 46
aggcgagtcg acgtttcaaa caatcatcaa gtcaggttga agatgcattt gaggtaaaga      60
tagaagc      67

<210> SEQ ID NO 47
<211> LENGTH: 67
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 47
aggcgagtcg acgtttcaaa caatcatcaa gtcaggttga agatgcatgt gaggtaaaga    60
tagaagc                                                              67

<210> SEQ ID NO 48
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 48
aggcgagtcg acgtttcaaa caatcatcaa gtcaggttga agatgcatca gaggtaaaga    60
tagaagc                                                              67

<210> SEQ ID NO 49
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 49
aggcgagtcg acgtttcaaa caatcatcaa gtcaggttga agatgcatcg gaggtaaaga    60
tagaagc                                                              67

<210> SEQ ID NO 50
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 50
aggcgagtcg acgtttcaaa caatcatcaa gtcaggttga agatgcatgc caggtaaaga    60
tagaagc                                                              67

<210> SEQ ID NO 51
<211> LENGTH: 67
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 51
aggcgagtcg acgtttcaaa caatcatcaa gtcaggttga agatgcataa caggtaaaga    60
tagaagc                                                              67

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 52

```
aatgcagaat tcacaacacc actagcaggt ttg                                    33
```

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 53

```
aggcgagtcg acgtttcaaa caatcatcaa gtcagg                                 36
```

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 54

```
gccgaccggt agatctgaca aagcagcatt ag                                     32
```

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 55

```
cggcggtacc gctctctctc tccccttgc                                         29
```

<210> SEQ ID NO 56
<211> LENGTH: 5757
<212> TYPE: DNA
<213> ORGANISM: Oryza sativa

<400> SEQUENCE: 56

```
gatgccgtcg tatactcgta tgctgctgcc ttctatcgat cgatcaaact cccgagtccc       60
gagtccgagt cgcgtacgcg tgccggcgtg cggcgccgtg tgcgtccgca gttcgcaggc      120
cgcacgctcg gctgggctgg ctctagtcct actgggcttc tcgcaggtgg gggcccctgg      180
aaattggggg cccccctgcga tcgcccagct cgctctccgc gatcgacggg cctgggtagt      240
tagcaccttg atcctggtta ccactacctc tcgagtagat ggcatctact cgagaggtag      300
tggcagccaa gaattaacaa cataggccgg tgatgacgag ggagacagca ccatcggtga      360
ccatgggaac aagggagagg gcattaatgg aagtgttgct aacccaaagc tactactatg      420
aagataagta ctgtaggatt agtactctca actcagtggc atgctttat ccaaaaggct       480
acaatcaaga gttgcttcca gggcaaatgc ccttagttat gctttttttt tttaatcccc      540
aatgggctct cctctgtaga attttcttcc aactttatcc tctttggagt ttggcctaac      600
ctaacatcta attatatagt taccatcgta caacgttact ctcaagcgag aaccaagtcg      660
tcatagttcc aaagtaggaa aagttattcc attaattagc tactcggtcc atgcaaagat      720
cgtaagcata tttattttat catcgagacc aagaaaaaaa attaactcat tcgatttgta      780
ctcccatgta acaaactttt tcatatgcat gcaaagggt tggagaatgc atggcagctc       840
aagtttcggt caacaattta atcatacacg gtaaaacgaa aagagactct cttcatttaa      900
```

-continued

```
ggctcggatg catggagact atatgaataa gctcatctca tttggaaaaa aataatcaaa      960
acaatgaaat atgcttaata catttggatt tggatggagt atctccctat gacgaaagag     1020
acgagggatt gcctacttct ttccacatca acctttgaag gctatggcag agctacattt     1080
gcagcgcagc ctctctgcat gatttcttac tagataggat taagtttcaa gagttaattt     1140
cttgtactct tgggcgatcc atgctgtcaa atcagcaact aacgaggcat aatctcgatc     1200
actagctctg atctgatctt cagctagcgc cggcgagctg cagaggtctc catccatggc     1260
gccggcggtc attgcatcgc agggtgtcat catgcggtcc ctgacgagca agctcgactc     1320
gctgctgctg cagccgccgg agccgccgcc gcctgcgcaa ccgtcgtcgc tgcggaaggg     1380
ggagaggaag aagatcctcc tcctcagagg cgatctccga cacctgctag atgactacta     1440
cctcctcgtg gagccgccgt cagacaccgc gccaccgcca gactcgacgg cggcgtgctg     1500
ggctaaggag gttcgcgagc tctcctacga cgtcgacgac ttcctcgacg agctaacgac     1560
ccagctcctc caccaccgcg gcggcggcga tggcagtagc actgctggtg ccaagaagat     1620
gatcagcagc atgatcgcgc ggcttcgagg ggagcttaac cggcggcggt ggatcgccga     1680
cgaggtcacc ctgttcaggg cccgcgtgaa ggaggccatt cgccgccacg agagctacca     1740
tcttggcagg cgcacctcga gctcgaggcc gagagaagaa gacgacgacg acgatcgcga     1800
ggactccgcc ggcaacgaac gccgccggtt tctgtcgctg acgttcggga tggacgacgc     1860
tgctgtgcac ggccagctcg ttggtaggga tatttcgatg caaaagctcg tccggtggct     1920
ggccgacggc gagccgaagc tcaaggtggc ttccattgtt ggatccggag gtgttggcaa     1980
gacgacgctg gccacagaat tctatcgtct gcatggccgg cggttggatg cgccgttcga     2040
ctgccgggct ttcgtgcgga cgccccggaa gcctgacatg acgaagatcc tcaccgacat     2100
gctgtcacag ctgcggccac aacatcagca tcagtcttcg gatgtttggg aggttgatcg     2160
actccttgaa actatccgga cgcatttgca agataaaagg taattcatgt ctacatctat     2220
ctctagtatt tttttcatga atttacaaac tattttctca aatttcccct tttttatcct     2280
tcatatagta attaagttag taactataca tatgaattta atttactcga caatgccaat     2340
aatatttaa attacttta tagtgtcctc tattattaaa tacaattcga tcgagccatg      2400
aatcatactg gtaatctaaa caattattat acccacctca ttctactaac agcaattgag     2460
ttgttaatat aaatagatat ggtctattgc atgaaaaaat aaaggtaaag tgtttacatt     2520
atttctacta ctagtagcag aactacaaag ttgtttgtat ttttaattat taaatgtaaa     2580
tgaaagtaca tgtttcatac ccttgttatt tttttaggcg actaaactac tagtacatta     2640
tttctactac tagtagaaca actacaaagt tgtttgtatt tttaattact aaatgtaaat     2700
gaaagtacat gcttcatacc cttgttataa tattttagac taaactacca caatggcatg     2760
ttaacttata gcagtaagtt gtaatttatt ttcttttcat tttctcagtt gttacaagaa     2820
ctttttttta cttaataaaa aatagtcgta agggcctccc ttgttcggtc aaaaaagaat     2880
tagactaaac tcaatcgtat ttgtacataa acaaaattta aaatataact aaaacgaaac     2940
agtgataaaa atggtgcaat ttaactgctg cctcttgttt taatgtctga caatgttgat     3000
tttgtatata tgtttggcca tttatttat tcaatttttt tacaaatatg aaaaatataa      3060
tatgtgctta aattactttt aatgataaaa taaatttaag aaaatgataa ttatattttt     3120
aataagatgg atgatctaac atatatatgt ccaaaagttt gacatcaaac attaaaaaca     3180
agagagagta tttgcttagg agtacgtgtc tttttccatg ccttagaaca ggtacaatag     3240
caggttataa gctaggccaa acatatttta aagagatata ggaagagaga gaagagcagc     3300
```

```
agcctacaga tctgtagcca gctgcagcac ggactctaag acgtaatgtg tgtatgacag   3360
gtaggaccaa gtattaatag tatagtaagc aactattgta tgaattggct atttggctct   3420
agatgatttg gagctagtag tcggctatac tattaaactt gctcttagat atgtggttaa   3480
atttaatttc tgaaatttac aagatataga acatgtcttc accatgtttg caaagttgat   3540
aaaatgaaat tgcactcaac tttttaaatt cagcatgcta tcccacgtat agcttttaa    3600 atatgattta tttttcgta cattagaagt ttaatgttta cgaagtacta aatgttctgc    3660
aggtacttca tcataattga agatttatgg gcttcatcaa tgtgggatat tgttagccgt   3720
ggtttgcctg ataataatag ttgcagtaga atactaataa caacagaaat tgaacctgta   3780
gctttggcat gctgtggata taactcagag cacattatta agattgatcc actgggtgat   3840
gatgtctcaa gtcaattgtt tttcagtgga gttgttggcc aaggaaatga atttcctgga   3900
catcttactg aagtttctca tgacatgata aaaaaatgtg gtggcttgcc actagcaata   3960
actataacag ccagacattt taaaagccag ctgttagatg gaatgcagca atggaatcac   4020
atacaaaaat cattgactac ttccaatttg aagaaaatc ctactttgca ggggatgagg     4080
caagtactca accttattta caataatctt cctcattgtt tgaaagcatg tctgttatac   4140
cttagcatct acaaagagga ctacataatt aggaaggcca acttggtgag gcaatggatg   4200
gctgaaggtt tcatcaattc catagaaaat aaagtcatgg aagaagttgc agggaactat   4260
tttgatgaac ttgttggtag gggcctggtc caaccagtag atgttaactg caaaaatgag   4320
gtattgtcat gtgtagtgca ccacatggta ttaaatttca tcaggtgtaa gtcaatagag   4380
gagaatttca gcattacatt ggatcattct cagacgacag taagacatgc tgacaaggtt   4440
cgccgactct cgcttcactt cagcaatgca catgatacaa caccactagc aggtttgaga   4500
ctctcacaag ttcgatcgat ggcatttttc ggacaagtca agtgtatgcc ttccattgca   4560
gattataggc ttcttcgagt tctgattctt tgttttggg ctgatcaaga gaaaacaagc    4620
tatgacctca caagcatttt tgaactgtta caactgagat atctgaagat aacaggtaat   4680
atcacagtta aacttccaga gaagatccaa ggactacaac acttgcagac actggaagca   4740
gatgcaagag caactgctgt cctattggat attgttcata cacagtgttt gttgcacctt   4800
cgtcttgtac tacttgatct gctccctcac tgtcacaggt acatcttcac cagcatcccc   4860
aaatggactg gaaagctcaa caatctccgc atttaaaaca ttgcagtcat gcaaatttcc   4920
caggatgacc ttgacactct caaaggactg ggatctctca ctgctctttc gctgcttgtt   4980
cgaacagcgc ctgcgcaaag aatcgtcgct gcgaatgagg ggttcgggtc tctcaagtac   5040
ttcatgtttg tctgtacagc accatgcatg acttttgtgg aaggagcaat gccgagtgtg   5100
caaaggttaa atctaaggtt caatgccaac gagttcaagc agtatgactc taaggagaca   5160
gggttggaac acttggtcgc ccttgcagag atctctgcaa gaattggggg cactgatgat   5220
gatgaatcaa acaaaactga agtggagtct gccttgagga ctgcaattcg caagcatccg   5280
acgccgagca ctcttatggt tgatatacaa tgggtggatt ggatctttgg tgctgaaggg   5340
agagacttgg atgaagattt ggcacaacaa gatgatcacg ggtatggatt tttcattcta   5400
ttcccaggtt acaacttaca aggattattg agcttctttc tttctctgcc gtggcttcta   5460
tcttaacctg ctatgcatct tcaacctgac ttgatgattg tttgaaacca attttaatgg   5520
aagttaaatg ttattgttgt gaccctgaat caggttttgt atgctaccgg aatcctcttc   5580
acgtcttcag agtagaggta attttgtttc ttgtcatttt acagttacag ttcatcttct   5640
```

-continued

```
taaggaatta atgggaggtc ctatattttc tcgggtacct agaaggtgtg gttcctagtc    5700
ttacctcctt aagaaccgta gaatgttggc cctaacactt ggatcaaaga acgaaag       5757

<210> SEQ ID NO 57
<211> LENGTH: 5222
<212> TYPE: DNA
<213> ORGANISM: Oryza sativa

<400> SEQUENCE: 57
gaattctaag caaaactctc ctccaatgct ccctttcttt ttcaagttct cgttgggcaa      60
ctttatcaat tgtttgattc ttttgcatcc taagacgcaa ttcataccat gtggacatat     120
ttgtgacatg ctctctacta attcatgctc tttaagtcta ttagcaagat gattccagtc     180
attgacaccg tcatttgtta gctgacttct cacaagcccc tttctcaata atttgcaaca     240
aaaacaaaat actttgtcaa gctctttgct gtaaacaagc cattccctgt cacacttctc     300
tccatttgag agaactttag tgtatgatga tgcaagaaac cttctagaca aattgtctct     360
gggaccatgc tcaatagaca aatctctttt agggcccttt tgcaataaaa tatcaatcat     420
tttaggatca agtccatccc aagttcttgg atcaaacata tcaggtcgaa agaaacatt      480
atcgtcggcg tcgtcagcaa tattttcctc attccttca ctggcaagat cacggccttc      540
atcggcaaga tcatggccaa tgtctccatc aacattttcc tctactgcgt catcactttc     600
ggcaatatta gcatcaacct ctgccatatc atcactaata tcgtcttcaa tattagcatt     660
tggagtttct ctcaaaaaaa atttatcaag agcaccctt tgagattgag ctactgcttc      720
tagtcttctt ctcttctggc gttttcagc gccagaatca tacttcctat ttctagagga     780
catgatcgct tcacttgatg aattgaggat tgaccgaccg aactgctata gtactgtatt     840
ctttctgttt aataaaaaac taaagtaact tcagtgattt taatcaaaca tgaactgatc     900
aattaaattt aatttaattt acattgtaca tttgtactca caaagtcaca atggagaaca     960
ggagaagccg agaaggtccg acggcagcgg cggcgtggcg tcggcggcgg cggtggcgcg    1020
gacggcagcg gcggcacggc gtcggccgga cggcagcggc gttcggctcg gctgcctgga    1080
ttggatggcg aggcgacgag acgacgaggc ggcgagagcg ctaggagcct agggctgcga    1140
gtcgtgcgat gcgaggacag aaaccgaagc gatgccgtcg tatactcgta tgctgctgcc    1200
ttctatcgat cgatcaaact cccgagtccc gagtccgagt cgcgtacgcg tgccggcgtg    1260
cggcgccgtg tgcgtccgca gttcgcaggc cgcacgctcg gctgggctgg ctctagtcct    1320
actgggcttc tcgcaggtgg gggcccctgg aaattggggg cccctgcga tcgcccagct     1380
cgctctccgc gatcgacggg cctgggtagt tagcaccttg atcctggtta ccactacctc    1440
tcgagtagat ggcatctact cgagaggtag tggcagccaa gaattaacaa cataggccgg    1500
tgatgacgag ggagacagca ccatcggtga ccatgggaac aagggagagg gcattaatgg    1560
aagtgttgct aacccaaagc tactactatg aagataagta ctgtaggatt agtactctca    1620
actcagtggc atgcttttat ccaaaaggct acaatcaaga gttgcttcca gggcaaatgc    1680
ccttagttat gctttttttt tttaatcccc aatgggctct cctctgtaga attttcttcc    1740
aactttatcc tctttggagt ttggcctaac ctaacatcta attatatagt taccatcgta    1800
caacgttact ctcaagcgag aaccaagtcg tcatagttcc aaagtaggaa aagttattcc    1860
attaattagc tactcggtcc atgcaaagat cgtaagcata tttattttat catcgagacc    1920
aagaaaaaaa attaactcat tcgatttgta ctcccatgta acaaactttt tcatatgcat    1980
gcaaagggt tggagaatgc atggcagctc aagtttcggt caacaattta atcatacacg     2040
```

```
gtaaaacgaa aagagactct cttcatttaa ggctcggatg catggagact atatgaataa    2100
gctcatctca tttggaaaaa aataatcaaa acaatgaaat atgcttaata catttggatt    2160
tggatggagt atctccctat gacgaaagag acgagggatt gcctacttct ttccacatca    2220
acctttgaag gctatggcag agctacattt gcagcgcagc ctctctgcat gatttcttac    2280
tagataggat taagtttcaa gagttaattt cttgtactct tgggcgatcc atgctgtcaa    2340
atcagcaact aacgaggcat aatctcgatc actagctctg atctgatctt cagctagcgc    2400
cggcgagctg cagaggtctc catccatggc gccggcggtc attgcatcgc agggtgtcat    2460
catgcggtcc ctgacgagca agctcgactc gctgctgctg cagccgccgg agccgccgcc    2520
gcctgcgcaa ccgtcgtcgc tgcggaaggg ggagaggaag aagatcctcc tcctcagagg    2580
cgatctccga cacctgctag atgactacta cctcctcgtg gagccgccgt cagacaccgc    2640
gccaccgcca gactcgacgg cggcgtgctg ggctaaggga gttcgcgagc tctcctacga    2700
cgtcgacgac ttcctcgacg agctaacgac ccagctcctc caccaccgcg gcggcggcga    2760
tggcagtagc actgctggtg ccaagaagat gatcagcagc atgatcgcgc ggcttcgagg    2820
ggagcttaac cggcggcggt ggatcgccga cgaggtcacc ctgttcaggg cccgcgtgaa    2880
ggaggccatt cgccgccacg agagctacca tcttggcagg cgcacctcga gctcgaggcc    2940
gagagaagaa gacgacgacg acgatcgcga ggactccgcc ggcaacgaac gccgccggtt    3000
tctgtcgctg acgttcggga tggacgacgc tgctgtgcac ggccagctcg ttggtaggga    3060
tatttcgatg caaaagctcg tccggtggct ggccgacggc gagccgaagc tcaaggtggc    3120
ttccattgtt ggatccggag gtgttggcaa gacgacgctg gccacagaat tctatcgtct    3180
gcatggccgg cggttggatg cgccgttcga ctgccgggct ttcgtgcgga cgccccggaa    3240
gcctgacatg acgaagatcc tcaccgacat gctgtcacag ctgcggccac aacatcagca    3300
tcagtcttcg gatgtttggg aggttgatcg actccttgaa actatccgga cgcatttgca    3360
agataaaagg tacttcatca taattgaaga tttatgggct tcatcaatgt gggatattgt    3420
tagccgtggt ttgcctgata taatagttg cagtagaata ctaataacaa cagaaattga    3480
acctgtagct ttggcatgct gtggatataa ctcagagcac attattaaga ttgatccact    3540
gggtgatgat gtctcaagtc aattgttttt cagtggagtt gttggccaag gaaatgaatt    3600
tcctggacat cttactgaag tttctcatga catgataaaa aaatgtggtg gcttgccact    3660
agcaataact ataacagcca gacattttaa aagccagctg ttagatggaa tgcagcaatg    3720
gaatcacata caaaaatcat tgactacttc caatttgaag aaaaatccta ctttgcaggg    3780
gatgaggcaa gtactcaacc ttatttacaa taatcttcct cattgtttga agcatgtct    3840 gttataccctt agcatctaca aagaggacta cataattagg aaggccaact tggtgaggca    3900
atggatggct gaaggtttca tcaattccat agaaaataaa gtcatggaag aagttgcagg    3960
gaactatttt gatgaacttg ttggtagggg cctggtccaa ccagtagatg ttaactgcaa    4020
aaatgaggta ttgtcatgtg tagtgcacca catggtatta aatttcatca ggtgtaagtc    4080
aatagaggag aatttcagca ttacattgga tcattctcag acgacagtaa gacatgctga    4140
caaggttcgc cgactctcgc ttcacttcag caatgcacat gatacaacac cactagcagg    4200
tttgagactc tcacaagttc gatcgatggc atttttcgga caagtcaagt gtatgccttc    4260
cattgcagat tataggcttt ttcgagttct gattctttgt ttttgggctg atcaagaaa    4320 aacaagctat gacctcacaa gcatttttga actgttacaa ctgagatatc tgaagataac    4380
```

-continued

```
aggtaatatc acagttaaac ttccagagaa gatccaagga ctacaacact tgcagacact    4440
ggaagcagat gcaagagcaa ctgctgtcct attggatatt gttcatacac agtgtttgtt    4500
gcaccttcgt cttgtactac ttgatctgct ccctcactgt cacaggtaca tcttcaccag    4560
catccccaaa tggactggaa agctcaacaa tctccgcatt taaacattg cagtcatgca     4620 aatttcccag gatgaccttg acactctcaa aggactggga tctctcactg ctctttcgct    4680
gcttgttcga acagcgcctg cgcaaagaat cgtcgctgcg aatgaggggt tcgggtctct    4740
caagtacttc atgtttgtct gtacagcacc atgcatgact tttgtggaag gagcaatgcc    4800
gagtgtgcaa aggttaaatc taaggttcaa tgccaacgag ttcaagcagt atgactctaa    4860
ggagacaggg ttggaacact tggtcgccct tgcagagatc tctgcaagaa ttgggggcac    4920
tgatgatgat gaatcaaaca aaactgaagt ggagtctgcc ttgaggactg caattcgcaa    4980
gcatccgacg ccgagcactc ttatggttga tatacaatgg gtggattgga tctttggtgc    5040
tgaagggaga gacttggatg aagatttggc acaacaagat gatcacgggt atggattttt    5100
cattctattc ccaggttaca acttacaagg attattgagc ttctttcttt ctctgccgtg    5160
gcttctatct ttacctgcta tgcatcttca acctgacttg atgattgttt gaaaccaagc    5220
tt                                                                   5222
```

<210> SEQ ID NO 58
<211> LENGTH: 928
<212> TYPE: PRT
<213> ORGANISM: Oryza sativa

<400> SEQUENCE: 58

```
Met Ala Pro Ala Val Ile Ala Ser Gln Gly Val Ile Met Arg Ser Leu
1               5                   10                  15

Thr Ser Lys Leu Asp Ser Leu Leu Gln Pro Glu Pro Pro
            20                  25                  30

Pro Ala Gln Pro Ser Ser Leu Arg Lys Gly Glu Arg Lys Lys Ile Leu
        35                  40                  45

Leu Leu Arg Gly Asp Leu Arg His Leu Leu Asp Asp Tyr Tyr Leu Leu
    50                  55                  60

Val Glu Pro Pro Ser Asp Thr Ala Pro Pro Asp Ser Thr Ala Ala
65                  70                  75                  80

Cys Trp Ala Lys Glu Val Arg Glu Leu Ser Tyr Asp Val Asp Asp Phe
                85                  90                  95

Leu Asp Glu Leu Thr Thr Gln Leu Leu His His Arg Gly Gly Gly Asp
            100                 105                 110

Gly Ser Ser Thr Ala Gly Ala Lys Lys Met Ile Ser Ser Met Ile Ala
        115                 120                 125

Arg Leu Arg Gly Glu Leu Asn Arg Arg Trp Ile Ala Asp Glu Val
    130                 135                 140

Thr Leu Phe Arg Ala Arg Val Lys Glu Ala Ile Arg Arg His Glu Ser
145                 150                 155                 160

Tyr His Leu Gly Arg Arg Thr Ser Ser Ser Arg Pro Arg Glu Glu Asp
                165                 170                 175

Asp Asp Asp Asp Arg Glu Asp Ser Ala Gly Asn Glu Arg Arg Phe
            180                 185                 190

Leu Ser Leu Thr Phe Gly Met Asp Asp Ala Ala Val His Gly Gln Leu
        195                 200                 205

Val Gly Arg Asp Ile Ser Met Gln Lys Leu Val Arg Trp Leu Ala Asp
    210                 215                 220
```

```
Gly Glu Pro Lys Leu Lys Val Ala Ser Ile Val Gly Ser Gly Gly Val
225                 230                 235                 240

Gly Lys Thr Thr Leu Ala Thr Glu Phe Tyr Arg Leu His Gly Arg Arg
            245                 250                 255

Leu Asp Ala Pro Phe Asp Cys Arg Ala Phe Val Arg Thr Pro Arg Lys
        260                 265                 270

Pro Asp Met Thr Lys Ile Leu Thr Asp Met Leu Ser Gln Leu Arg Pro
    275                 280                 285

Gln His Gln His Gln Ser Ser Asp Val Trp Glu Val Asp Arg Leu Leu
290                 295                 300

Glu Thr Ile Arg Thr His Leu Gln Asp Lys Arg Tyr Phe Ile Ile Ile
305                 310                 315                 320

Glu Asp Leu Trp Ala Ser Ser Met Trp Asp Ile Val Ser Arg Gly Leu
                325                 330                 335

Pro Asp Asn Asn Ser Cys Ser Arg Ile Leu Ile Thr Thr Glu Ile Glu
            340                 345                 350

Pro Val Ala Leu Ala Cys Cys Gly Tyr Asn Ser Glu His Ile Ile Lys
        355                 360                 365

Ile Asp Pro Leu Gly Asp Asp Val Ser Ser Gln Leu Phe Phe Ser Gly
370                 375                 380

Val Val Gly Gln Gly Asn Glu Phe Pro Gly His Leu Thr Glu Val Ser
385                 390                 395                 400

His Asp Met Ile Lys Lys Cys Gly Gly Leu Pro Leu Ala Ile Thr Ile
                405                 410                 415

Thr Ala Arg His Phe Lys Ser Gln Leu Leu Asp Gly Met Gln Gln Trp
            420                 425                 430

Asn His Ile Gln Lys Ser Leu Thr Thr Ser Asn Leu Lys Lys Asn Pro
        435                 440                 445

Thr Leu Gln Gly Met Arg Gln Val Leu Asn Leu Ile Tyr Asn Asn Leu
    450                 455                 460

Pro His Cys Leu Lys Ala Cys Leu Leu Tyr Leu Ser Ile Tyr Lys Glu
465                 470                 475                 480

Asp Tyr Ile Ile Arg Lys Ala Asn Leu Val Arg Gln Trp Met Ala Glu
                485                 490                 495

Gly Phe Ile Asn Ser Ile Glu Asn Lys Val Met Glu Val Ala Gly
            500                 505                 510

Asn Tyr Phe Asp Glu Leu Val Gly Arg Gly Leu Val Gln Pro Val Asp
        515                 520                 525

Val Asn Cys Lys Asn Glu Val Leu Ser Cys Val Val His His Met Val
530                 535                 540

Leu Asn Phe Ile Arg Cys Lys Ser Ile Glu Glu Asn Phe Ser Ile Thr
545                 550                 555                 560

Leu Asp His Ser Gln Thr Thr Val Arg His Ala Asp Lys Val Arg Arg
                565                 570                 575

Leu Ser Leu His Phe Ser Asn Ala His Asp Thr Thr Pro Leu Ala Gly
            580                 585                 590

Leu Arg Leu Ser Gln Val Arg Ser Met Ala Phe Phe Gly Gln Val Lys
        595                 600                 605

Cys Met Pro Ser Ile Ala Asp Tyr Arg Leu Leu Arg Val Leu Ile Leu
    610                 615                 620

Cys Phe Trp Ala Asp Gln Glu Lys Thr Ser Tyr Asp Leu Thr Ser Ile
625                 630                 635                 640
```

```
Phe Glu Leu Leu Gln Leu Arg Tyr Leu Lys Ile Thr Gly Asn Ile Thr
                645                 650                 655
Val Lys Leu Pro Glu Lys Ile Gln Gly Leu Gln His Leu Gln Thr Leu
            660                 665                 670
Glu Ala Asp Ala Arg Ala Thr Ala Val Leu Leu Asp Ile Val His Thr
        675                 680                 685
Gln Cys Leu Leu His Leu Arg Leu Val Leu Leu Asp Leu Leu Pro His
    690                 695                 700
Cys His Arg Tyr Ile Phe Thr Ser Ile Pro Lys Trp Thr Gly Lys Leu
705                 710                 715                 720
Asn Asn Leu Arg Ile Leu Asn Ile Ala Val Met Gln Ile Ser Gln Asp
                725                 730                 735
Asp Leu Asp Thr Leu Lys Gly Leu Gly Ser Leu Thr Ala Leu Ser Leu
            740                 745                 750
Leu Val Arg Thr Ala Pro Ala Gln Arg Ile Val Ala Ala Asn Glu Gly
        755                 760                 765
Phe Gly Ser Leu Lys Tyr Phe Met Phe Val Cys Thr Ala Pro Cys Met
    770                 775                 780
Thr Phe Val Glu Gly Ala Met Pro Ser Val Gln Arg Leu Asn Leu Arg
785                 790                 795                 800
Phe Asn Ala Asn Glu Phe Lys Gln Tyr Asp Ser Lys Glu Thr Gly Leu
                805                 810                 815
Glu His Leu Val Ala Leu Ala Glu Ile Ser Ala Arg Ile Gly Gly Thr
            820                 825                 830
Asp Asp Asp Glu Ser Asn Lys Thr Glu Val Glu Ser Ala Leu Arg Thr
        835                 840                 845
Ala Ile Arg Lys His Pro Thr Pro Ser Thr Leu Met Val Asp Ile Gln
    850                 855                 860
Trp Val Asp Trp Ile Phe Gly Ala Glu Gly Arg Asp Leu Asp Glu Asp
865                 870                 875                 880
Leu Ala Gln Gln Asp Asp His Gly Tyr Gly Phe Phe Ile Leu Phe Pro
                885                 890                 895
Gly Tyr Asn Leu Gln Gly Leu Leu Ser Phe Phe Leu Ser Leu Pro Trp
            900                 905                 910
Leu Leu Ser Leu Pro Ala Met His Leu Gln Pro Asp Leu Met Ile Val
        915                 920                 925

<210> SEQ ID NO 59
<211> LENGTH: 881
<212> TYPE: DNA
<213> ORGANISM: Magnaporthe grisea

<400> SEQUENCE: 59 atgcttttt  attcattatt  ttttttcac  accgttgcga  tttcggcctt  caccaacatt    60 ggcaccttt  cacacccagt  ttacgattac  aatccaattc  caaaccatat  ccacggagat   120 ttaaaaggc  gggcttatat  tgaacgctat  tcccaatgtt  cagattcgca  ggcctccgaa   180
attcgtgccg  cgctaaaaag  gtaaattgaa  actctttaaa  acaaattcgg  aaaacaatgt   240
taaatatttt  gtttagttgc  gccgagctcg  cctcgtgggg  ctatcacgcc  gttaaaagta   300
acaatcggtt  atttaaatta  atctttaaaa  ctgacagcac  agatattcaa  aactgggttc   360
aaaataattt  taacgaaatt  tacaaggaat  gtaacaggga  cgcggacgaa  atttctctaa   420
cctgccacga  taaaaatgtt  tatacgtgcg  tccgagaagg  agttcataat  ttggcgtatg   480
cacttattaa  cgaaaagaa  attgttatat  gccctccttt  cttcaacaac  cccgtaaaca   540
```

```
gcagggaaat tactgccggt aaccaagata caattatatt acatgaaatg gtgcatataa      600
ttttaagtaa gtttgctttt acaaattgat aaaacattta caaagtttta tttataaaaa      660
ttttcaaaaa ctaaaaattc aaattttat ttagaagagt ggaaagatta tggttgcgaa       720
tgggatggga ttcacaagta agttgtcgaa aaacaaaatg ctgaatgttg ttttatattg      780
ataaattcta attaatatta agattggata gtacagaaag tattaaaaac cccgacagtt      840
atgctatttt tgcacaatgt gcacgttata aatattgtta a                          881
```

<210> SEQ ID NO 60
<211> LENGTH: 5696
<212> TYPE: DNA
<213> ORGANISM: Artificial Sequence
<220> FEATURE:
<223> OTHER INFORMATION: Description of Artificial Sequence:Chimeric Gene

<400> SEQUENCE: 60

```
gaattctaag caaaactctc ctccaatgct ccctttcttt ttcaagttct cgttgggcaa       60
ctttatcaat tgtttgattc ttttgcatcc taagacgcaa ttcataccat gtggacatat      120
ttgtgacatg ctctctacta attcatgctc tttaagtcta ttagcaagat gattccagtc      180
attgacaccg tcatttgtta gctgacttct cacaagcccc tttctcaata atttgcaaca      240 aaacaaaat actttgtcaa gctctttgct gtaaacaagc cattccctgt cacacttctc       300
tccatttgag agaactttag tgtatgatga tgcaagaaac cttctagaca aattgtctct      360
gggaccatgc tcaatagaca aatctctttt agggcccttt tgcaataaaa tatcaatcat      420
tttaggatca agtccatccc aagttcttgg atcaaacata tcaggtcgaa aagaaacatt      480
atcgtcggcg tcgtcagcaa tattttcctc attaccttca ctggcaagat cacggccttc      540
atcggcaaga tcatggccaa tgtctccatc aacattttcc tctactgcgt catcactttc      600
ggcaatatta gcatcaacct ctgccatatc atcactaata tcgtcttcaa tattagcatt      660
tggagtttct ctcaaaaaaa atttatcaag agcacccttt tgagattgag ctactgcttc      720
tagtcttctt ctcttctggc gttttcagc gccagaatca tacttcctat ttctagagga       780
catgatcgct tcacttgatg aattgaggat tgaccgaccg aactgctata gtactgtatt      840
cttttcgttt aataaaaaac taaagtaact tcagtgattt taatcaaaca tgaactgatc      900
aattaaattt aatttaattt acattgtaca tttgtactca caaagtcaca atggagaaca      960
ggagaagccg agaaggtccg acggcagcgg cggcgtggcg tcggcggcgg cggtggcgcg     1020
gacggcagcg gcggcacggc gtcggccgga cggcagcggc gttcggctcg gctgcctgga     1080
ttggatggcg aggcgacgag acgacgaggc ggcgagagcg ctaggagcct agggctgcga     1140
gtcgtgcgat gcgaggacag aaaccgaagc gatgccgtcg tatactcgta tgctgctgcc     1200
ttctatcgat cgatcaaact cccgagtccc gagtccgagt cgcgtacgcg tgccggcgtg     1260
cggcgccgtg tgcgtccgca gttcgcaggc cgcacgctcg gctgggctgg ctctagtcct     1320
actgggcttc tcgcaggtgg gggcccctgg aaattggggg cccctgcga tcgcccagct      1380 cgctctccgc gatcgacggg cctgggtagt tagcaccttg atcctggtta ccactacctc     1440
tcgagtagat ggcatctact cgagaggtag tggcagccaa gaattaacaa cataggccgg     1500
tgatgacgag ggagacagca ccatcggtga ccatgggaac aagggagagg gcattaatgg     1560
aagtgttgct aacccaaagc tactactatg aagataagta ctgtaggatt agtactctca     1620
actcagtggc atgcttttat ccaaaaggct acaatcaaga gttgcttcca gggcaaatgc     1680
```

```
ccttagttat gctttttttt tttaatcccc aatgggctct cctctgtaga attttcttcc    1740
aactttatcc tctttggagt ttggcctaac ctaacatcta attatatagt taccatcgta    1800
caacgttact ctcaagcgag aaccaagtcg tcatagttcc aaagtaggaa aagttattcc    1860
attaattagc tactcggtcc atgcaaagat cgtaagcata tttattttat catcgagacc    1920
aagaaaaaaa attaactcat tcgatttgta ctcccatgta acaaactttt tcatatgcat    1980 gcaaagggt tggagaatgc atggcagctc aagtttcggt caacaattta atcatacacg     2040
gtaaaacgaa aagagactct cttcatttaa ggctcggatg catggagact atatgaataa    2100
gctcatctca tttggaaaaa aataatcaaa acaatgaaat atgcttaata catttggatt    2160
tggatggagt atctccctat gacgaaagag acgaggatt gcctacttct ttccacatca     2220
acctttgaag gctatggcag agctacattt gcagcgcagc ctctctgcat gatttcttac    2280
tagataggat taagtttcaa gagttaattt cttgtactct tgggcgatcc atgctgtcaa    2340
atcagcaact aacgaggcat aatctcgatc actagctctg atctgatctt cagctagcgc    2400
cggcgagctg cagaggtctc catccatggc gccggcggtc attgcatcgc agggtgtcat    2460
catgcggtcc ctgacgagca agctcgactc gctgctgctg cagccgccgg agccgccgcc    2520
gcctgcgcaa ccgtcgtcgc tgcggaaggg ggagaggaag aagatcctcc tcctcagagg    2580
cgatctccga cacctgctag atgactacta cctcctcgtg gagccgccgt cagacaccgc    2640
gccaccgcca gactcgacgg cggcgtgctg ggctaaggag gttcgcgagc tctcctacga    2700
cgtcgacgac ttcctcgacg agctaacgac ccagctcctc caccaccgcg gcggcggcga    2760
tggcagtagc actgctggtg ccaagaagat gatcagcagc atgatcgcgc ggcttcgagg    2820
ggagcttaac cggcggcggt ggatcgccga cgaggtcacc ctgttcaggg cccgcgtgaa    2880
ggaggccatt cgccgccacg agagctacca tcttggcagg cgcacctcga gctcgaggcc    2940
gagagaagaa gacgacgacg acgatcgcga ggactccgcc ggcaacgaac gccgccggtt    3000
tctgtcgctg acgttcggga tggacgacgc tgctgtgcac ggccagctcg ttggtaggga    3060
tatttcgatg caaaagctcg tccggtggct ggccgacggc gagccgaagc tcaaggtggc    3120
ttccattgtt ggatccggag gtgttggcaa gacgacgctg gccacagaat tctatcgtct    3180
gcatggccgg cggttggatg cgccgttcga ctgccgggct ttcgtgcgga cgccccggaa    3240
gcctgacatg acgaagatcc tcaccgacat gctgtcacag ctgcggccac aacatcagca    3300
tcagtcttcg gatgtttggg aggttgatcg actccttgaa actatccgga cgcatttgca    3360
agataaaagg tacttcatca taattgaaga tttatgggct tcatcaatgt gggatattgt    3420
tagccgtggt ttgcctgata ataatagttg cagtagaata ctaataacaa cagaaattga    3480
acctgtagct ttggcatgct gtggatataa ctcagagcac attattaaga ttgatccact    3540
gggtgatgat gtctcaagtc aattgttttt cagtggagtt gttggccaag gaatgaatt     3600 tcctggacat cttactgaag tttctcatga catgataaaa aaatgtggtg gcttgccact    3660
agcaataact ataacagcca gacattttaa aagccagctg ttagatggaa tgcagcaatg    3720
gaatcacata caaaaatcat tgactacttc caatttgaag aaaaatccta ctttgcaggg    3780
gatgaggcaa gtactcaacc ttatttacaa taatcttcct cattgtttga agcatgtct     3840 gttataccttt agcatctaca aagaggacta cataattagg aaggccaact tggtgaggca   3900
atggatggct gaaggtttca tcaattccat agaaaataaa gtcatggaag aagttgcagg    3960
gaactatttt gatgaacttg ttggtagggg cctggtccaa ccagtagatg ttaactgcaa    4020
```

| | | | | |
|---|---|---|---|---|
| aaatgaggta | ttgtcatgtg | tagtgcacca | catggtatta | aatttcatca ggtgtaagtc | 4080 |
| aatagaggag | aatttcagca | ttacattgga | tcattctcag | acgacagtaa gacatgctga | 4140 |
| caaggttcgc | cgactctcgc | ttcacttcag | caatgcacat | gatacaacac cactagcagg | 4200 |
| tttgagactc | tcacaagttc | gatcgatggc | attttcgga | caagtcaagt gtatgccttc | 4260 |
| cattgcagat | tataggcttt | ttcgagttct | gattctttgt | ttttgggctg atcaagagaa | 4320 |
| aacaagctat | gacctcacaa | gcatttttga | actgttacaa | ctgagatatc tgaagataac | 4380 |
| aggtaatatc | acagttaaac | ttccagagaa | gatccaagga | ctacaacact tgcagacact | 4440 |
| ggaagcagat | gcaagagcaa | ctgctgtcct | attggatatt | gttcatacac agtgtttgtt | 4500 |
| gcaccttcgt | cttgtactac | ttgatctgct | ccctcactgt | cacaggtaca tcttcaccag | 4560 |
| catccccaaa | tggactggaa | agctcaacaa | tctccgcatt | ttaaacattg cagtcatgca | 4620 |
| aatttcccag | gatgaccttg | acactctcaa | aggactggga | tctctcactg ctctttcgct | 4680 |
| gcttgttcga | acagcgcctg | cgcaaagaat | cgtcgctgcg | aatgagggt tcgggtctct | 4740 |
| caagtacttc | atgtttgtct | gtacagcacc | atgcatgact | tttgtggaag gagcaatgcc | 4800 |
| gagtgtgcaa | aggttaaatc | taaggttcaa | tgccaacgag | ttcaagcagt atgactctaa | 4860 |
| ggagacaggg | ttggaacact | tggtcgccct | tgcagagatc | tctgcaagaa ttgggggcac | 4920 |
| tgatgatgat | gaatcaaaca | aaactgaagt | ggagtctgcc | ttgaggactg caattcgcaa | 4980 |
| gcatccgacg | ccgagcactc | ttatggttga | tatacaatgg | gtggattgga tctttggtgc | 5040 |
| tgaagggaga | gacttggatg | aagatttggc | acaacaagat | gatcacgggt atggattttt | 5100 |
| cattctattc | ccaggttaca | acttacaagg | attattgagc | ttctttcttt ctctgccgtg | 5160 |
| gcttctatct | ttacctgcta | tgcatcttca | acctgacttg | atgattgttt gaaaccaagc | 5220 |
| ttcccatggt | gacgtaccgg | tagatctgac | aaagcagcat | tagtccgttg atcggtggaa | 5280 |
| gaccactcgt | cagtgttgag | ttgaatgttt | gatcaataaa | atacggcaat gctgtaaggg | 5340 |
| ttgtttttta | tgccattgat | aatacactgt | actgttcagt | tgttgaactc tatttcttag | 5400 |
| ccatgccaag | tgcttttctt | attttgaata | acattacagc | aaaaagttga ttagactgtg | 5460 |
| ttcggcgttc | ccctaaatt | tctccccta | tatctcactc | acttgtcaca tcagcgttct | 5520 |
| ctttccccct | atatctccac | gctctacagc | agttccacct | atatcaaacc tctatacccc | 5580 |
| accacaacaa | tattatatac | tttcatcttc | aactaactca | tgtaccttcc aattttttct | 5640 |
| actaataatt | atttacgtgc | acagaaactt | aggcaaggga | gagagagagc ggtacc | 5696 |